(12) United States Patent
Harper et al.

(10) Patent No.: US 10,126,299 B2
(45) Date of Patent: Nov. 13, 2018

(54) AMPLIFICATION OF BIOLOGICAL TARGETS VIA ON-CHIP CULTURE FOR BIOSENSING

(71) Applicant: National Technology & Engineering Solutions of Sandia, LLC, Albuquerque, NM (US)

(72) Inventors: Jason C. Harper, Rio Rancho, NM (US); Thayne L. Edwards, Bend, OR (US); Bryan Carson, Tijeras, NM (US); Melissa Finley, Albuquerque, NM (US); William Arndt, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/820,836

(22) Filed: Nov. 22, 2017

(65) Prior Publication Data
US 2018/0095083 A1    Apr. 5, 2018

Related U.S. Application Data

(62) Division of application No. 14/157,378, filed on Jan. 16, 2014, now Pat. No. 9,857,370.
(Continued)

(51) Int. Cl.
*B01L 3/00*    (2006.01)
*G01N 33/569*    (2006.01)
(Continued)

(52) U.S. Cl.
CPC .. *G01N 33/56911* (2013.01); *B01L 3/502738* (2013.01); *F16K 31/086* (2013.01);
(Continued)

(58) Field of Classification Search
None
See application file for complete search history.

(56) References Cited

U.S. PATENT DOCUMENTS 2,347,434 A    4/1944    Reichert et al.
2,590,856 A    4/1952    Greenspan et al.
(Continued)

FOREIGN PATENT DOCUMENTS

| EP | 1688479 A1 | 8/2006 |
|---|---|---|
| WO | WO 2011/021008 A1 | 2/2011 |
| WO | WO 2015/013004 A1 | 1/2015 |

OTHER PUBLICATIONS

Burkhart G, "Sandia Labs works on terror detectors," KRQE.com, available at http://www.krqe.com/news/local/central/sandia-labs-works-on-terror-detectors, published and updated Apr. 22, 2013 (last accessed Dec. 12, 2013) (2 pages).
(Continued)

*Primary Examiner* — Rebecca L Martinez
(74) *Attorney, Agent, or Firm* — Helen S. Baca

(57) ABSTRACT

The present invention, in part, relates to methods and apparatuses for on-chip amplification and/or detection of various targets, including biological targets and any amplifiable targets. In some examples, the microculture apparatus includes a single-use, normally-closed fluidic valve that is initially maintained in the closed position by a valve element bonded to an adhesive coating. The valve is opened using a magnetic force. The valve element includes a magnetic material or metal. Such apparatuses and methods are useful for in-field or real-time detection of targets, especially in limited resource settings.

16 Claims, 15 Drawing Sheets

Related U.S. Application Data

(60) Provisional application No. 61/870,841, filed on Aug. 28, 2013, provisional application No. 61/857,029, filed on Jul. 22, 2013.

(51) Int. Cl.
*F16K 31/08* (2006.01)
*F16K 99/00* (2006.01)

(52) U.S. Cl.
CPC ........ *F16K 99/003* (2013.01); *F16K 99/0046* (2013.01); *B01L 2300/0663* (2013.01); *B01L 2300/0816* (2013.01); *B01L 2300/0887* (2013.01); *B01L 2400/0406* (2013.01); *B01L 2400/0633* (2013.01); *F16K 2099/0084* (2013.01); *Y10T 137/87917* (2015.04)

(56) References Cited

U.S. PATENT DOCUMENTS

| | | |
|---|---|---|
| 2,609,391 A | 9/1952 | Greenspan et al. |
| 4,051,058 A | 9/1977 | Bowing et al. |
| 5,656,302 A | 8/1997 | Cosentino et al. |
| 6,372,895 B1 | 4/2002 | Bentsen et al. |
| 6,566,508 B2 | 5/2003 | Bentsen et al. |
| 8,257,964 B2 | 9/2012 | Hung et al. |
| 8,278,045 B2 | 10/2012 | Rothschild et al. |
| 9,389,231 B2 | 7/2016 | Edwards et al. |
| 2006/0073484 A1 | 4/2006 | Mathies et al. |
| 2009/0036324 A1 | 2/2009 | Fan et al. |
| 2009/0053732 A1 | 2/2009 | Vermesh et al. |
| 2009/0251155 A1 | 10/2009 | Wang et al. |
| 2009/0317896 A1 | 12/2009 | Yoo |
| 2010/0021558 A1 | 1/2010 | Dada et al. |
| 2010/0243078 A1 | 9/2010 | Yoo |
| 2010/0288949 A1 | 11/2010 | Yoo |
| 2011/0129850 A1 | 6/2011 | Tseng et al. |
| 2011/0250609 A1 | 10/2011 | Rothschild et al. |
| 2012/0214189 A1 | 8/2012 | Shuler et al. |
| 2012/0231976 A1 | 9/2012 | Wu et al. |
| 2013/0224729 A1 | 8/2013 | Church et al. |

OTHER PUBLICATIONS

Edwards TL, "Elucidating the role of interfacial materials properties in microfluidic packages," *Technical Sandia Report* SAND2013-0369, Jan. 2013 (62 pages), issued by Sandia National Laboratories, operated for the United States Department of Energy by Sandia Corporation.

Harper JC et al., "Laser machined plastic laminates: towards portable diagnostic devices for use in low resource environments," *Electroanalysis* 2015;27:2503-12.

Harper JC et al., "Magnetic-adhesive based valves for microfluidic devices used in low-resource settings," *Lab Chip* 2016;16:4142-51.

Harper JC et al., "Portable diagnostic device for the detection of *Bacillus anthracis* in ultra-low resource environments," Abstract No. 0778, for Miniaturized Systems for Chemistry & Life Sciences, MicroTAS 2014 held Oct. 26-30, 2014 in San Antonio, TX, Report No. SAND2014-4042C (2 pages).
Harper JC et al., "Selective immobilization of DNA and antibody probes on electrode arrays: simultaneous electrochemical detection of DNA and protein on a single platform," Langmuir Ju.l 31, 2007;23(16):8285-7.
Holinka S, "Pocket-sized anthrax detector aids global agriculture," Apr. 17, 2014 (available at https://www.eurekalert.org/pub_releases/2014-04/dnl-pad041714.php, last accessed Nov. 22, 2014.
Niemz A et al., "Point-of-care nucleic acid testing for infectious diseases," Trends Biotechnol. 2011;29(5):240-50.
Polsky R et al., "Electrically addressable diazonium-functionalized antibodies for multianalyte electrochemical sensor applications," Biosens. Bioelectron. Jan. 18, 2008;23(6):757-64.
Polsky R et al., "Reagentless electrochemical immunoassay using electrocatalytic nanoparticle-modified antibodies," Chem. Commun. (Camb.) Jul. 14, 2007;(26):2741-3.
Ross L, "Harper's device would detect anthrax," *Rio Rancho Observer*, Apr. 21, 2013 (2 pages) (available at http://www.rrobserver.com/news/local/article_251d0a1a-a93e-11e2-9h17-001a4bcf887a.html, last accessed Dec. 12, 2013.
Sandia National Laboratories, "LDRD impacts on Sandia Biosciences: Biothreats to biofuels," *Sandia Report* SAND2013-2788P, 2013 (36 pages) (available at http://www.sandia.gov/research/laboratory_directed_research/_assets/documents/LLDRD_Impacts_Biosciences_SAND2013-2788P.pdf, last accessed Dec. 12, 2013).
International Preliminary Report on Patentability (IPRP) for International Application No. PCT/US2014/044806, issuance date of Iprp of Jan. 26, 2016 (13 pages).
International Search Report (ISR) for International Application No. PCT/US2014/044806, dated Oct. 27, 2014 (3 pages).
Written Opinion (WO) of the International Searching Authority for International Application No. PCT/US2014/044806, dated Oct. 27, 2014 (12 pages).
Response to Written Opinion for International Application No. PCT/US2014/044806, dated Dec. 17, 2014 (4 pages).
Office Action dated Jul. 27, 2015 in U.S. Appl. No. 14/157,335 (30 pages).
Reply filed on Oct. 23, 2015 to Office Action dated Jul. 27, 2015 in U.S. Appl. No. 14/157,335 (19 pages).
Office Action dated Nov. 17, 2015 in U.S. Appl. No. 14/157,335 (17 pages).
Reply filed on Feb. 12, 2016 to Office Action dated Nov. 17, 2015 in U.S. Appl. No. 14/157,335 (17 pages).
Applicant-initiated Interview Summary dated Feb. 5, 2016 in U.S. Appl. No. 14/157,335 (3 pages).

Fig. 12A

Sterilization solution for use following assay 0.5 mm glass beads to aid mixing prior to exposing LFA strip

Fig. 12B

B. anthracis Detected

Assay Control

Commercially available LFA strip

AMPLIFICATION OF BIOLOGICAL TARGETS VIA ON-CHIP CULTURE FOR BIOSENSING

CROSS-REFERENCE TO RELATED APPLICATION

This application is a divisional of prior U.S. application Ser. No. 14/157,378, filed Jan. 16, 2014, which in turn claims the benefit of U.S. Provisional Application Nos. 61/857,029, filed Jul. 22, 2013, and 61/870,841, filed Aug. 28, 2013, each of which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

BACKGROUND OF THE INVENTION

Miniaturized systems can be useful for detecting various analytes, contaminants, and toxins. In particular, such systems can allow for real-time or in-field detection of a target, while minimizing sample and reagent consumption. Point-of-care testing has wide applicability, not only in diagnostic fields, but also in detecting pathogens or genetic modifications in agricultural settings, as well as assessing biological and chemical threats in environmental screenings.

Despite significant progress in the development of biosensor technologies, the utility of many assays remains limited. Generally, this is due to the inability of these assays to detect the biological target at or below the infectious dose (commonly $10^2$-$10^3$ cells or spores). Also, some sensors lack the sensitivity and/or specificity required for detection of the desired target.

For use in remote or low resource settings, simpler sensor systems are desired. For instance, such systems can include simplified modes of operation, reduced power use, and low production costs. When toxic agents are being detected, another benefit includes single-use systems that could be safely disposed. Accordingly, more components to implement such systems are needed.

SUMMARY OF THE INVENTION

The present invention features apparatuses having a magnetically actuated valve and methods of their use. One example embodiment of the invention is a single-use, normally-closed fluidic valve, which is opened using a magnetic force. The valve includes a valve seat (including an opening) and a valve element, which closes the opening of the valve seat.

In one example, the valve seat is made from a thin laminate (approximately 0.5 to 1.0 mm thick) that separates two chambers (e.g., fluidic chambers) and is coated with adhesive. A hole cut into the laminate serves as a fluidic via between the chambers, which is temporarily sealed closed with a valve element affixed over the via and adhered to the adhesive of the laminate.

The valve element is composed of a material that responds to an applied magnetic field. For instance, such materials include a magnetic material or a metal. In one non-limiting use, the valve is opened by bringing an external magnet in proximity to the valve to provide a magnetic force that delaminates the valve from the adhesive coating. The external magnet is then physically moved to a location away from the via, which removes the valve opening the via for fluid flow between the chambers. In another embodiment, an integrated magnet is configured over the valve to provide an applied magnetic field to the valve element. In use, this integrated magnet is activated (e.g., by providing current to an integrated electromagnet) to apply the magnetic field, thereby opening the valve. To close the valve, the integrated magnet is deactivated (e.g., by removing current to the integrated electromagnet), thereby releasing the valve element.

In particular, the present device can provide enhanced detection of one or more targets. In particular, the device can be adapted to include one or more chambers or reservoirs that allow for amplification of the target. For instance, if the target is a bacterium, then the device can include an incubation reservoir or chamber for increasing the concentration of the bacteria in the test sample. In a similar manner, the concentration of any amplifiable target (e.g., a virus, a fungus, or a parasite) can be increased, as compared to that in the test sample. In this manner, amplification of the biological target prior to downstream biodetection can improve the detection limit, allowing existing biosensing technologies to effectively detect practical concentrations or levels of the biological target. Accordingly, also described herein are robust portable devices for amplification of biological targets facilitating subsequent biodetection.

Furthermore, such devices can be ultra-low cost, require no power or instrumentation to operate, and can be operated by individuals with little to no technical training. Exemplary self-contained credit-card sized devices can employ on-chip microculture methods to amplify bacteria prior to downstream detection, improving detection limits by more than four orders of magnitude, where detection from a $10^2$ spores/mL initial inoculum is demonstrated herein.

In one aspect, the invention features an apparatus (e.g., a fluidic, microculture, and/or multilevel apparatus) including a first reservoir including at least one first outlet; a first valve element; a first valve seat conformed to support the first valve element in a position that closes the first outlet; and a layer of adhesive deposited on at least a portion of the first valve seat such that the adhesive layer is effective to releasably bond to a surface of the first valve element when the first valve element is seated in the outlet-closed position. In some embodiments, the first valve element is responsive to an applied magnetic field (e.g., by an external source and/or an integrated source, such as any described herein) of sufficient strength by detaching from the first valve seat and undergoing a displacement that causes the first outlet to open.

In some embodiments, the reservoir (e.g., first, second, third, or other reservoir) has a branch conformed to receive the valve element (e.g., first, second, third, or other valve element) in a location laterally displaced from the valve seat (e.g., the corresponding first, second, third, or other valve seat).

In some embodiments, the first outlet leads to a receiving chamber (e.g., a reaction chamber, a sample chamber, an incubation chamber, a reagent chamber, a sterilization chamber, an assay chamber, and/or a waste chamber).

In other embodiments, the reservoir (e.g., first, second, third, or other reservoir) further includes at least one inlet (e.g., a chamber or a channel in fluidic communication with a sample port, a receiving chamber, a further channel).

In further embodiments, the apparatus includes a second reservoir including at least one (e.g., one, two, three, four, five, six, seven, eight, nine, ten, or more) second outlet(s); a second valve element; and a second valve seat conformed to support the second valve element in a position that closes at least one second outlet. In some embodiments, the second valve element is responsive to an applied magnetic field (e.g., by an external or integrated source) of sufficient strength by detaching from the second valve seat and undergoing a displacement that causes at least one second outlet to open.

In some embodiment, the apparatus includes a second layer of adhesive deposited on at least a portion of the second valve seat such that the second adhesive layer is effective to releasably bond to a surface of the second valve element when the second valve element is seated in the outlet-closed position.

In some embodiments, the first outlet leads to a third reservoir and the second outlet leads to the first reservoir; the first outlet leads to the second reservoir and the second outlet leads to a third reservoir; or both the first and second outlets lead to the third reservoir.

In another aspect, the invention features an apparatus (e.g., a fluidic, microculture, and/or multilevel apparatus) including: a first reservoir (e.g., in a first level) including at least one first outlet; a second reservoir (e.g., in a second level, where the second level is below the first level), where the first outlet is configured for fluidic communication between the first and second reservoirs; a first valve element; a first valve seat conformed to support the first valve element in a position that closes the first outlet; and a first layer of adhesive deposited on at least a portion of the first valve seat and configured to releasably bond to a surface of the first valve element when seated in the outlet-closed position. In some embodiments, the first valve element is responsive to an applied magnetic field of sufficient strength by detaching from the first valve seat and undergoing a displacement that causes the first outlet to open. In other embodiments, the apparatus is a microculture apparatus and further includes a cell media (e.g., a stabilized cell media optionally including one or more host cells) in the first reservoir.

In some embodiments, the apparatus further includes a third reservoir (e.g., in the second level) including a second outlet configured for fluidic communication between the first and third reservoirs; a second valve element; and a second valve seat conformed to support the second valve element in a position that closes the second outlet. In further embodiments, the second valve element is responsive to an applied magnetic field (e.g., by an external and/or integrated source) of sufficient strength by detaching from the second valve seat and undergoing a displacement that causes the second outlet to open. In other embodiments, the apparatus is a microculture apparatus and further includes a sterilization agent (e.g., a stabilized sterilization agent) in the third reservoir.

In some embodiments, the apparatus includes a first and/or second layer of adhesive that is deposited on at least a portion of the second valve seat and configured to releasably bond to a surface of the second valve element when seated in the outlet-closed position.

In yet another aspect, the invention features a method for operating a device (e.g., a fluidic device or any apparatus described herein), the method including applying a first magnetic field to a first valve element adhesively bonded to a first valve seat so as to produce a magnetic force configured to detach the first valve element from the first valve seat; and by application of the first magnetic field, breaking the adhesive bond between the first valve element and the first valve seat, thereby causing displacement of the first valve element that opens a first outlet from a first reservoir.

In some embodiments, the method includes, by opening the first outlet, causing a first substance (e.g., sample, reagent, gas, liquid, semi-solid, or solid) to move (e.g., flow) from the first reservoir into a chamber, where the first outlet is configured to provide fluidic communication between the first reservoir and the chamber. In particular embodiments, the method further includes shaking and/or tapping the device or apparatus.

In other embodiments, the method includes applying a second magnetic field to a second valve element adhesively bonded to a second valve seat so as to produce a magnetic force configured to detach the second valve element from the second valve seat; and by application of the second magnetic field, breaking the adhesive bond between the second valve element and the second valve seat, thereby causing displacement of the second valve element that opens a second outlet from a second reservoir. In some embodiments, the first and second magnetic fields are the same magnetic field. In other embodiments, the first and second magnetic fields are different magnetic fields.

In some embodiments, the method includes by opening the second outlet, causing a second substance (e.g., sample, reagent, gas, liquid, semi-solid, or solid) to move (e.g., flow) from the second reservoir into the first reservoir and/or the chamber; and/or causing the first liquid to flow from the first reservoir and/or the chamber into the second reservoir. In particular embodiments, the method further includes shaking and/or tapping the device or apparatus.

In another aspect, the invention features a method for amplifying and/or detecting a target in a sample, the method including: introducing the sample within a first reservoir of a first apparatus, where the first apparatus includes a first outlet in fluidic communication with the first reservoir (e.g., where the first apparatus is configured to allow for in-field or real-time detection of the target); and incubating the sample within the first reservoir, thereby amplifying the target within the sample and providing an amplified sample. In some embodiments, the sample includes an amplifiable target (e.g., a bacterium, a virus, a parasite, a protozoon, a helminth, or a fungus).

In some embodiments, the method includes opening the first outlet (e.g., after the introducing step, before the incubating step, or after the incubating step) by applying a magnetic field to a first valve element adhesively bonded to a first valve seat so as to produce a magnetic force configured to detach the first valve element from the first valve seat.

In another embodiment, the method further includes introducing the amplified sample within an assay chamber, where the first outlet leads to the assay chamber and the assay chamber is configured to include one or more detection agents (e.g., a dye, a particle, a marker, or a label, or any agent described herein) for identifying the target, thereby identifying whether or not the target is present within the sample. In particular embodiments, the method further includes shaking and/or tapping the device or apparatus.

In some embodiments, the assay chamber is provided in the first apparatus or in a second apparatus having an inlet in fluidic communication with the assay chamber (e.g., where the inlet is in fluidic communication with the first outlet and/or the second outlet in the first apparatus).

In some embodiments, the method further includes sterilizing the amplified sample during or after the incubation step, and/or after identifying the target. In further embodiments, the sterilizing step includes opening a second outlet in fluidic communication between a second reservoir and the assay chamber, by applying a magnetic field to a second valve element adhesively bonded to a second valve seat conformed to support the second valve element in a position that closes the second outlet, where the magnetic field produces a magnetic force configured to detach the second valve element from the second valve seat; and introducing a sterilization agent from the second reservoir into the assay chamber. In particular embodiments, the method further includes shaking and/or tapping the device or apparatus. In some embodiments, the fluidic communication between the second reservoir and the assay chamber occurs through an open passageway in the first reservoir.

In some embodiments, the method further includes measuring the presence of a detectable signal from the detection agent, e.g., by electrochemical, colorimetric, fluorescent, western blot, immunohistochemistry, immunoassay, immunochromatography, radio immunoassay, optical immunoassay, enzyme immunoassay, chemiluminescence, and/or electrochemiluminescence methods. In other embodiments, the measuring step includes detection by lateral flow assay and/or detection of a plurality of targets (e.g., one or more bacteria, viruses, parasites, protozoa, helminths, fungi, foodborne pathogens, weaponized pathogens, or any target described herein).

In any of the embodiments, the valve element (e.g., first, second, third, or any valve element) includes a magnetic material (e.g., a permanent magnet, a neodymium magnet, a samarium-cobalt magnet, a ferrite magnet, and/or an alnico magnet) and/or a metal (e.g., iron, nickel, cobalt, gadolinium, neodymium, samarium, steel, magnetite, a ferrite, as well other metals, alloys, or composites capable of being magnetized). In any of the embodiments, the first, second, third, or any valve element is a disk.

In any of the embodiments, the first, second, third, or any valve element is releasably bonded to a first valve seat by an adhesive layer or a portion thereof.

In any of the embodiments, two or more valve elements (e.g., first and second valve elements, first and third valve elements, second and third valve elements, etc.) actuate in the same direction or in different directions.

In any of the embodiments, the reservoir (e.g., first, second, third, or other reservoir) is a reaction chamber, a sample chamber, an incubation chamber, a reagent chamber, a sterilization chamber, an assay chamber, or a waste chamber.

In any of the embodiments, the reservoir (e.g., first, second, third, or other reservoir) includes, independently, one or more sterilization agents (e.g., stabilized sterilization agents, as described herein), detection agents (e.g., an electroactive or electrocatalytic detection agent), labels (e.g., an electroactive or electrocatalytic detection agent or label), amplifying agents, capture agents, cell media (e.g., stabilized sterilization agents, as described herein, and optionally including host cells), cells (e.g., living host cells for the target), detergents, surfactants, buffers, alcohols, preservatives, blocking agents, beads, or combinations thereof.

In any of the embodiments, the reservoir (e.g., first, second, third, or other reservoir) includes a sterilization agent (e.g., any described herein, including a stabilized sterilization agent or a sterilization agent in solid, semisolid, liquid, or gas form).

In any of the embodiments, the reservoir (e.g., first, second, third, or other reservoir) includes an inlet for introducing a sample, and the apparatus is completely sealed except for the inlet.

In any of the embodiments, the reservoir (e.g., first, second, third, or other reservoir) includes a cell medium (e.g., any described herein, including a stabilized cell medium, optionally including living host cells for the target).

In any of the embodiments, the reservoir (e.g., first, second, third, or other reservoir) is further conformed to contain a capillary bed for lateral flow assay.

In any of the embodiments, the apparatus, device, or method includes an integrated source (e.g., an integrated permanent magnet, a magnetic coil (e.g., a solenoid), a metallic element to attract the valve element, or an electromagnet) configured to provide the applied magnetic field to the valve element (e.g., first, second, third, or other valve element).

In any of the embodiments, the apparatus, device, or method is configured for detection of one, two, three, four, five, six, seven, eight, nine, ten, or more targets (e.g., any target described herein).

In any of the embodiments, the apparatus, device, or method includes in-field amplification and/or detection of one or more targets (e.g., amplification and/or detection of one or more targets in less than about 24 hours, 12 hours, 6 hours, 5 hours, 4 hours, 3 hours, 2 hours, 1 hour, 30 minutes, 20 minutes, or less, and optionally configured to use no or minimal power for detecting the target).

In any of the embodiments, the apparatus, device, or method includes real-time amplification and/or detection of one or more targets (e.g., amplification and/or detection of one or more targets in less than about 2 hours, 1 hour, 45 minutes, 30 minutes, 20 minutes, 15 minutes, 10 minutes, 5 minutes or less, and optionally configured to use no or minimal power for detecting the target).

In any of the embodiments, the apparatus, device, or method is configured to allow for amplification and/or detection in a resource limited environment (e.g., an environment having limited access to a lab and/or trained staff). In one non-limiting embodiment, the device includes one or more additional components (e.g., any described herein). In another non-limiting embodiment, the device includes one or more components selected from the group of a separation/extraction component, a heating component, a pump, a membrane, a multifunctional sensor, a light-emitting diode, an active circuit element, a passive circuit element, a power source, a photodiode, and a telemetry unit.

In any of the embodiments, the method includes use of any device or apparatus (e.g., fluidic, microculture, and/or multilevel apparatus) described herein.

Definitions

By "about" is meant +/−10% of the recited value.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

In FIG. 11B, the on-chip microculture chamber is filled with dye. The entire device is about the size of four stacked credit cards.

FIG. 12A-12B shows photographs of an exemplary B. anthracis detection device in use.

DETAILED DESCRIPTION OF THE INVENTION

Figure 1A:
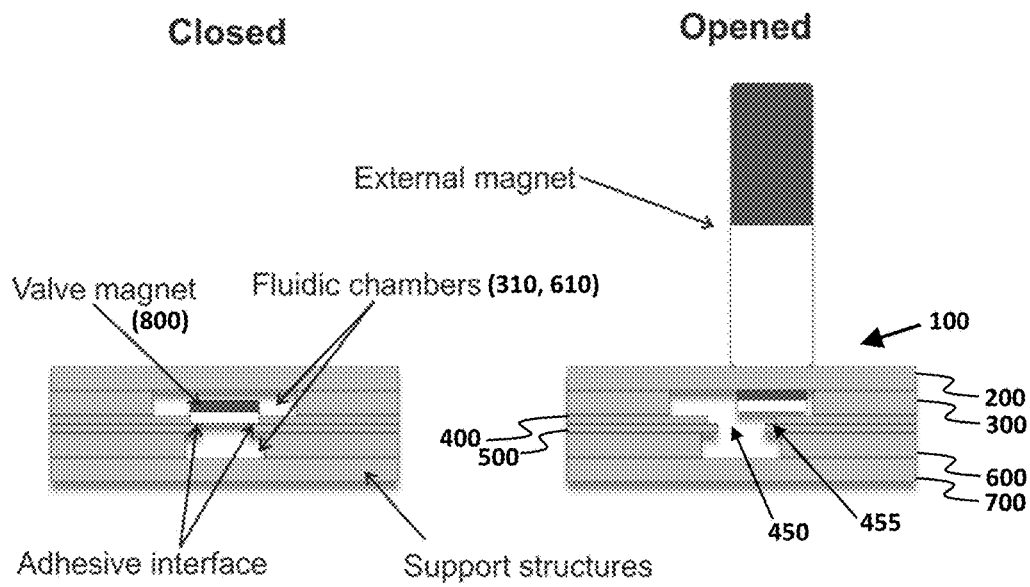
FIG. 1A provides a schematic, cross-sectional view of an apparatus 100 embodying an aspect of the present invention, including two fluidic chambers 310, 610 that intercommunicate through a via 450 that is sealable by a permanent magnet 800.

An exemplary principle of operation is illustrated in FIG. 1A, which provides a schematic, cross-sectional view of an apparatus 100 including two fluidic chambers 310, 610 that intercommunicate through a via 450 that is sealable by a permanent magnet 800. As shown in the figure by way of illustration only and not by way of limitation, the apparatus is constructed from six sheets, or laminae. The outer sheets 200, 700 are support structures. Each of the two sheets 300, 600 adjacent the respective outer sheets is perforated to provide fluidic chambers 310, 610.

The fifth and sixth sheets 400, 500 form an adjacent pair that is situated between the two perforated sheets 300, 600. The fifth and sixth sheets 400, 500 are perforated to provide a via 450 between the two fluidic chambers 310, 610. The perforations in the fifth and sixth sheets are exemplarily circular in cross section and concentric, with the lower perforation in sheet 500 of slightly smaller diameter than the upper perforation in sheet 400 so as to provide a shoulder 455 on which a valve element 800 rests.

In one embodiment, the valve element 800 is a permanent magnet that interfaces with the via 450. As can be seen in this exemplary device, the valve element 800 is a cylindrical magnet in order to interface with circular via 450. A skilled artisan would understand how to match the cross-sections of the valve element and the via to form a closed valve.

The upper surface of the shoulder 455 is coated with an adhesive layer. In the "valve closed" configuration, the valve element is seated on the shoulder 455 and temporarily bonded to the underlying layer by the adhesive (FIG. 1A, left). In that configuration, the valve element 800 seals the via 450 (in an outlet-closed position).

To actuate the valve, i.e., to transform it to the "valve open" configuration, an external permanent magnet is brought into proximity to the valve element (FIG. 1A, right). The force of magnetic attraction between the valve element 800 and the external magnet breaks the adhesive bond and lifts the valve element 800 off of its seat 455. Lateral motion of the external magnet then slides the valve element 800 to a neutral location where it no longer seals the via 450 (e.g., a recess or a corner of the chamber). Of course, the use of an external permanent magnet is merely illustrative and can be replaced, for example, by the electrical activation of magnetic coils or by using a metallic structure to which the valve element is attracted.

Figure 1B:
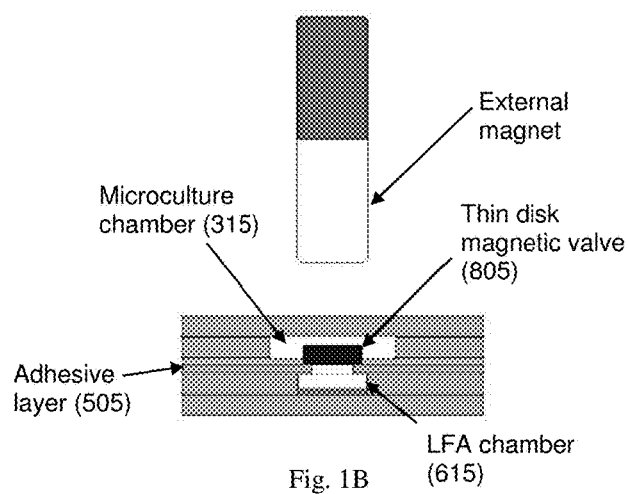
FIG. 1B is a schematic of magnetic valving used to control fluidic access between regions of an exemplary B. anthracis detection device.

FIG. 1B provides an exemplary device for use with a lateral flow assay (LFA). The device includes a microculture chamber 315 and an LFA chamber 615 having a capillary bed (shown as gray layer within chamber 615), where these two chambers are fluidically connected by an openable valve element 805. The valve seat includes an adhesive layer 505, as described herein.

Figure 2A:
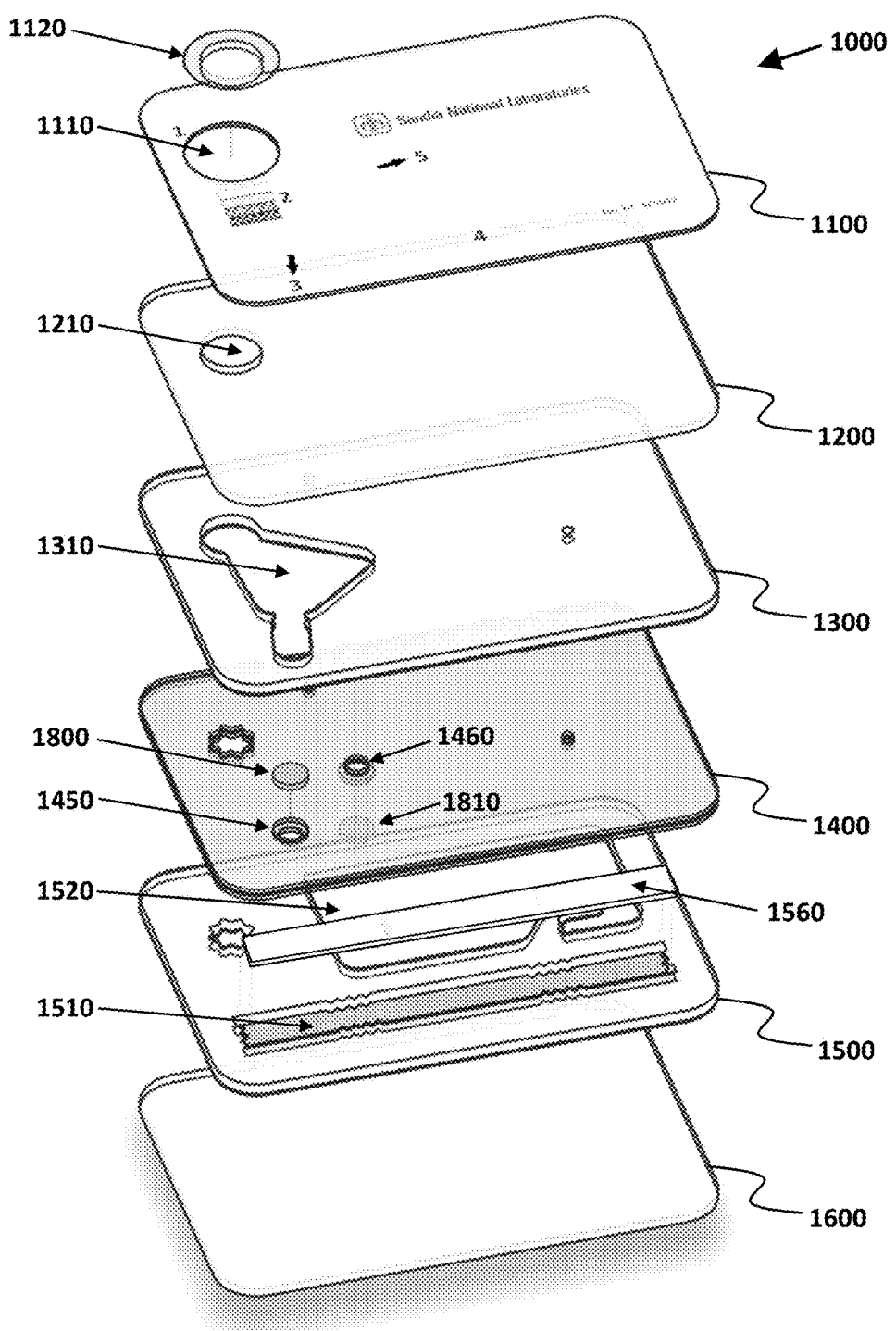
FIG. 2A provides a further, partially schematic, view of an apparatus 1000 embodying an aspect of the present invention. The view of FIG. 2A is an isometric, exploded view of an apparatus 1000 constructed in six layers 1100-1600 and containing two valves 1450/1800, 1460/1810 and three fluidic chambers 1310, 1510, 1520.

A more realistic, but still partially schematic, illustration of the invention is provided by FIG. 2A, which is an isometric, exploded view of an apparatus 1000 constructed in six layers 1100-1600 and containing two valves 1450/1800, 1460/1810 and three fluidic chambers 1310, 1510, 1520. As seen in the figure, the first (top) layer 1100 is a structural layer suitable for bearing printed legends and the like, and perforated with a fill hole 1110 that is sealable by a plug 1120. The second layer 1200 is likewise a structural layer perforated with a portion of the fill hole 1210. In the example illustrated, the plug 1120 has a wider top portion that seats in the perforation 1110 in the top layer 1100 and a narrower bottom portion that seats in the perforation 1210 in the second layer 1200.

The third layer 1300 is perforated to provide one of the fluidic chambers 1310, which in this example is a reservoir for a liquid sample, designated the sample chamber.

The fourth layer 1400 includes two vias 1450, 1460 and the seats for the two corresponding magnetic valve elements 1800, 1810. In some implementations, the fourth layer can be a composite layer made, e.g., from two, three, or more sheets, as described herein.

The fifth layer 1500 is perforated to provide the two further fluidic chambers 1510, 1520, whose bottoms are sealed by the sixth layer 1600, which is a structural layer. In this example, one of the fluidic chambers 1510 is designated as the Lateral Flow Assay (LFA) chamber, and the other is designated as the sterilization chamber 1520. In one exemplary embodiment, the LFA chamber is long and narrow (e.g., having a length to width ratio of 3:1, 4:1, 5:1, 6:1, 7:1, 8:1, 9:1, 10:1, 11:1, 12:1, or greater, as well as ranges therebetween). It is conformed for placement therein of a capillary bed 1560, such as a porous paper strip, for performing diagnostic procedures by immunochromatography or the like. Although the present invention is especially well suited for such uses, it has a wide range of potential applications that are not limited to the biomedical sphere. One of the two valves, designated the sample valve 1450/1800, is positioned so that when actuated, it admits liquid through its via 1450 from the sample chamber 1310 to one end of the LFA chamber 1510. In operation, the admitted sample liquid is absorbed by a portion of the capillary bed 1560 proximal the via 1450. From there, the sample liquid propagates by capillary action toward the other end of the capillary bed 1560.

As noted, the fifth layer 1500 is perforated to provide the LFA chamber 1510 and one further fluidic chamber, which is here designated the sterilization chamber 1520. The sterilization chamber 1520 is meant to hold a quantity of bleach or other sterilizing agent. The valve 1460/1810 for the sterilization chamber 1520 is aligned so that when actuated, it will admit the sterilizing agent through its via 1460 into the sample chamber 1310, then through the sample via 1450, from which it can also eventually penetrate into the LFA chamber 1510.

Figure 2B:
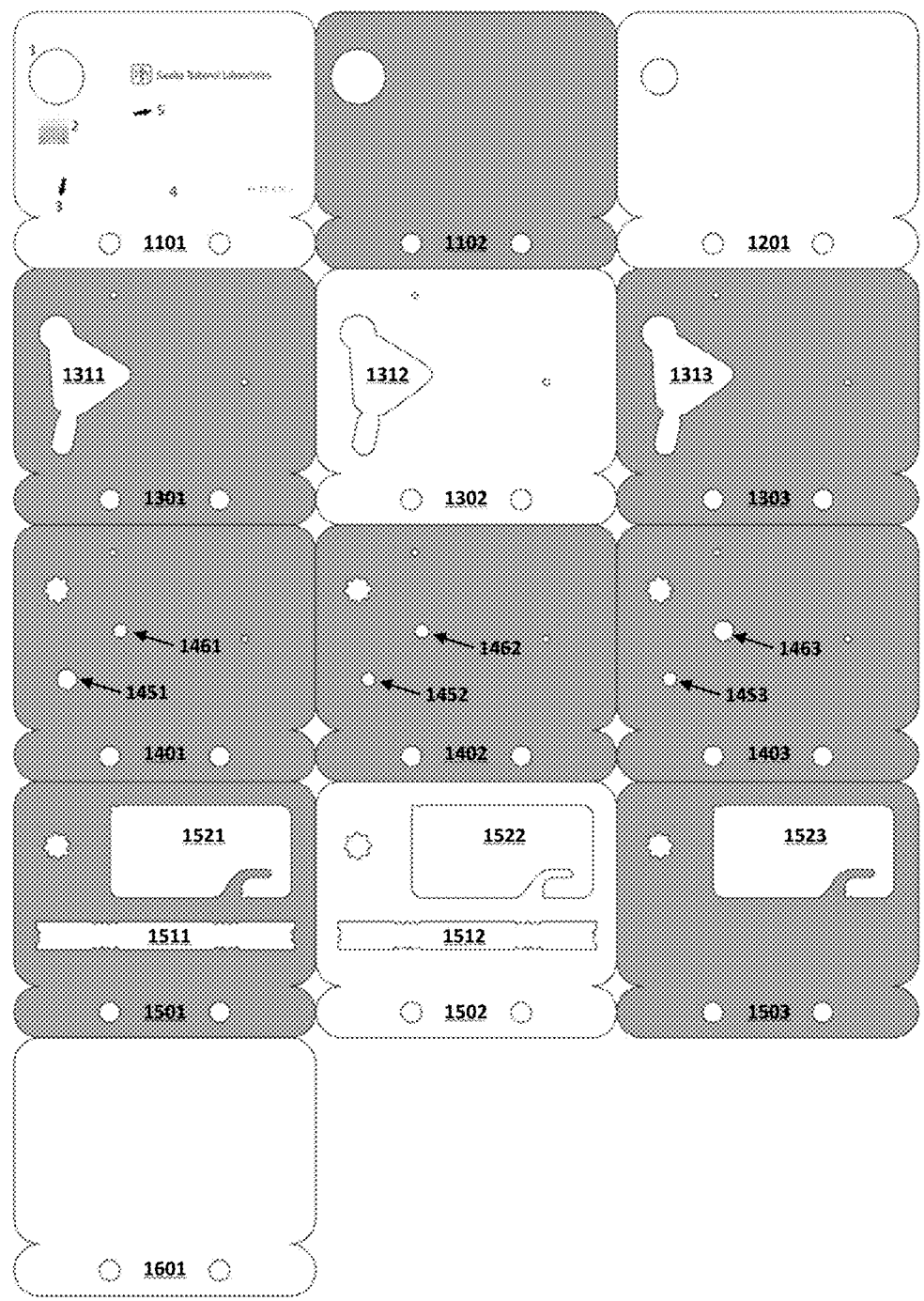
FIG. 2B provides a perspective, exploded view of the various layers of the apparatus in FIG. 2A.

FIG. 2B provides an exploded view showing that each of the six layers 1100-1600 can include further additional substrates or laminae. For instance, first layer 1100 can include a film substrate 1101 including labels and a first structural substrate 1102. The second layer is provided as a single substrate 1201. To laminate the first and second layers, an adhesive layer can be present either on the bottom of the first structural substrate 1102 or the top of the second substrate 1201. For any of the layers described herein, a skilled artisan would be able to design and construct one or more adhesive layers in a useful manner for assembling the apparatus.

The third layer 1300 can include multiple substrates, including an adhesive film 1301, a polymer substrate 1302, and another adhesive film 1303. As can be seen, each of these substrates can include an opening 1311-1313 to define a reservoir or sample chamber 1310 in the apparatus.

The fourth layer 1400 can include multiple substrates 1401-1403, which are designed to include valve seats for the magnetic valves. As can be seen, circular vias are provided in each of these substrates, where vias 1451-1453 form a first valve seat, and vias 1461-1463 form a second valve seat. The first valve seat is designed so that the via 1451 in the upper substrate 1401 is slightly larger than the vias 1452, 1453 in the lower substrates 1402, 1403. In this design, the first valve element would rest within via 1451 and the shoulder would be provided by the edge of vias 1452, 1453. In contrast, the second valve seat is designed so that the second valve element would rest within a via 1463 in the lower substrate 1403. For instance, the vias 1461, 1462 in the upper substrates 1401, 1402 are slightly smaller than the via 1463 in the lower substrate 1403. In this design, the second valve element would rest within via 1463 and the shoulder would be provided by the edge of vias 1461, 1462. Thus, the first valve element actuates into an open position by moving towards the top of the device, whereas the second valve element actuates into an open position by moving towards the bottom of the device. In this manner, a set of valves can be designed to actuate in different directions.

In some embodiments, substrate 1402 is an adhesive film or includes such a film, which provides an adhesive interface for both of the valves.

The fifth layer can include multiple substrates, including an adhesive film 1501, a structural substrate 1502, and another adhesive film 1503. As can be seen, adhesive film 1503 provides an exposed surface through the opening 1512, where this exposed surface can be useful for placing a capillary bed. These substrates can include an opening 1521-1523 to define a reservoir or sterilization chamber 1520 in the apparatus, as well as another opening 1511, 1512 to define the reaction chamber or LFA chamber 1510. Finally, the last layer 1600 can include a structural substrate 1601.

In some implementations, it may be useful to conform the reservoirs with side branches into which the released valve element can be directed by lateral movement of the external or integrated magnetic source. Such placement of the valve element can be advantageous in order to prevent it from subsequently interfering with flow through the vias. Exemplary side branches can be included in the sample chamber (see, e.g., the lower left side of the sample chamber 1311 in FIG. 2B, which provides an elongated branch that extends past the reaction chamber 1511 when the device is laminated) and/or in the sterilization chamber (see, e.g., the lower right side of the sterilization chamber 1521 in FIG. 2B, which provides a constricted side branch to place the valve element after opening the valve). In some other implementations, mutual repulsion between the respective valve elements may be sufficient to prevent them from blocking the vias, especially if the chamber thickness is too small to permit the valve elements to flip over.

An operative prototype was produced that was about 2.75 inches long, about 1.875 inches wide, and about 0.331 inches thick. Further miniaturization is possible. Miniaturization will ultimately be limited by the desired adhesion between the valve element and the valve seat, which for a given adhesive and given processing conditions will decrease as the contact area decreases, and by the viscosities or granularity of the various fluids and agents, which will lead to greater flow resistance as the vias and reservoirs become more constricted. The diminution of adhesive force can be compensated by increased time and pressure in the assembly process up to a saturation point beyond which further increases will not be beneficial. The increase in flow resistance might, in some implementations, be compensated by active pumping, e.g., through manually operated plungers or bellows, or through the motion of a massive free-body ram driven by shaking the device.

FIGS. 3-8 are based on schematics of prototype devices of the kind illustrated in FIG. 2A-2B in various stages of operation. The sample chamber 2310 is initially filled with an aqueous solution of blue food coloring, visible as the gray liquid in the figures. The sterilization chamber 2520 is initially filled with an aqueous bleach solution, which upon intermixing will decolorize the dyed solution.

Figure 3:
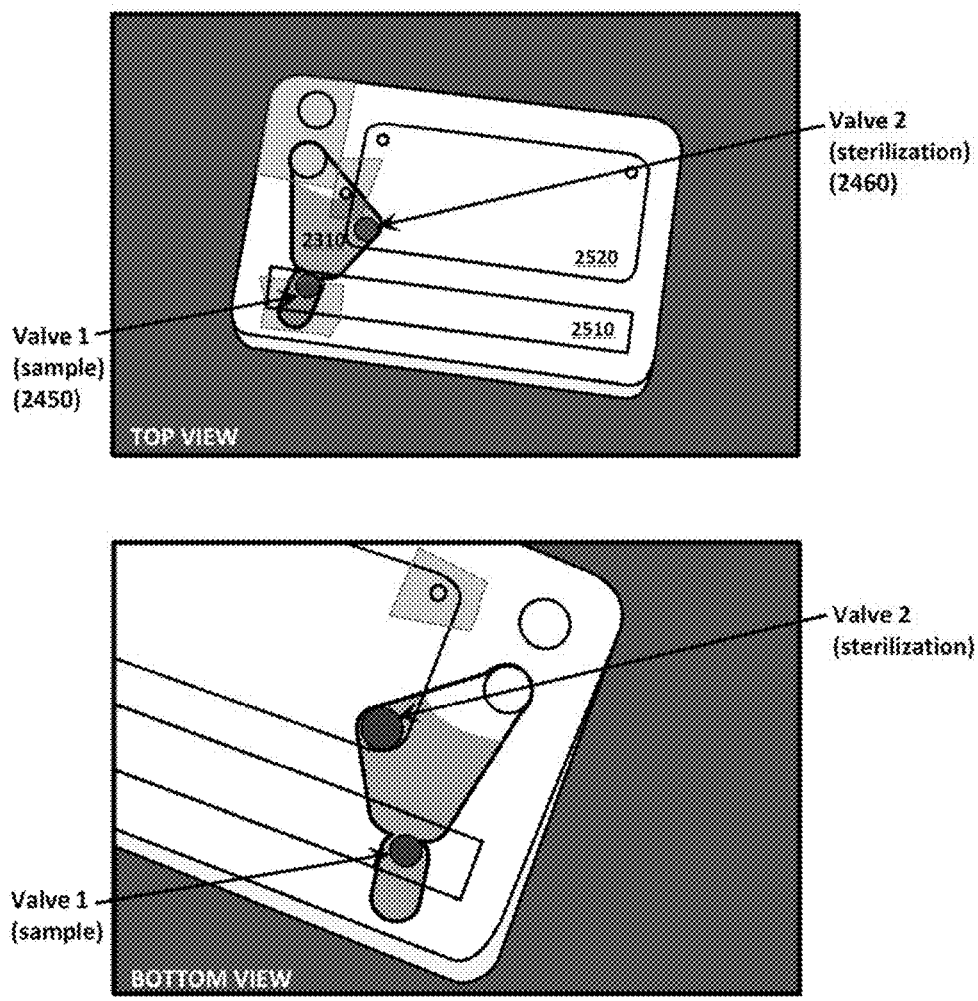
FIG. 3 provides top and bottom view schematics of an exemplary device prior to opening of the valves. The exemplar device includes a sample chamber 2310, a sterilization chamber 2520, a lateral flow assay (LFA) chamber 2510, a first valve (sample valve or "Valve 1") 2450, and a second valve (sterilization valve or "Valve 2") 2460.
Figure 4:
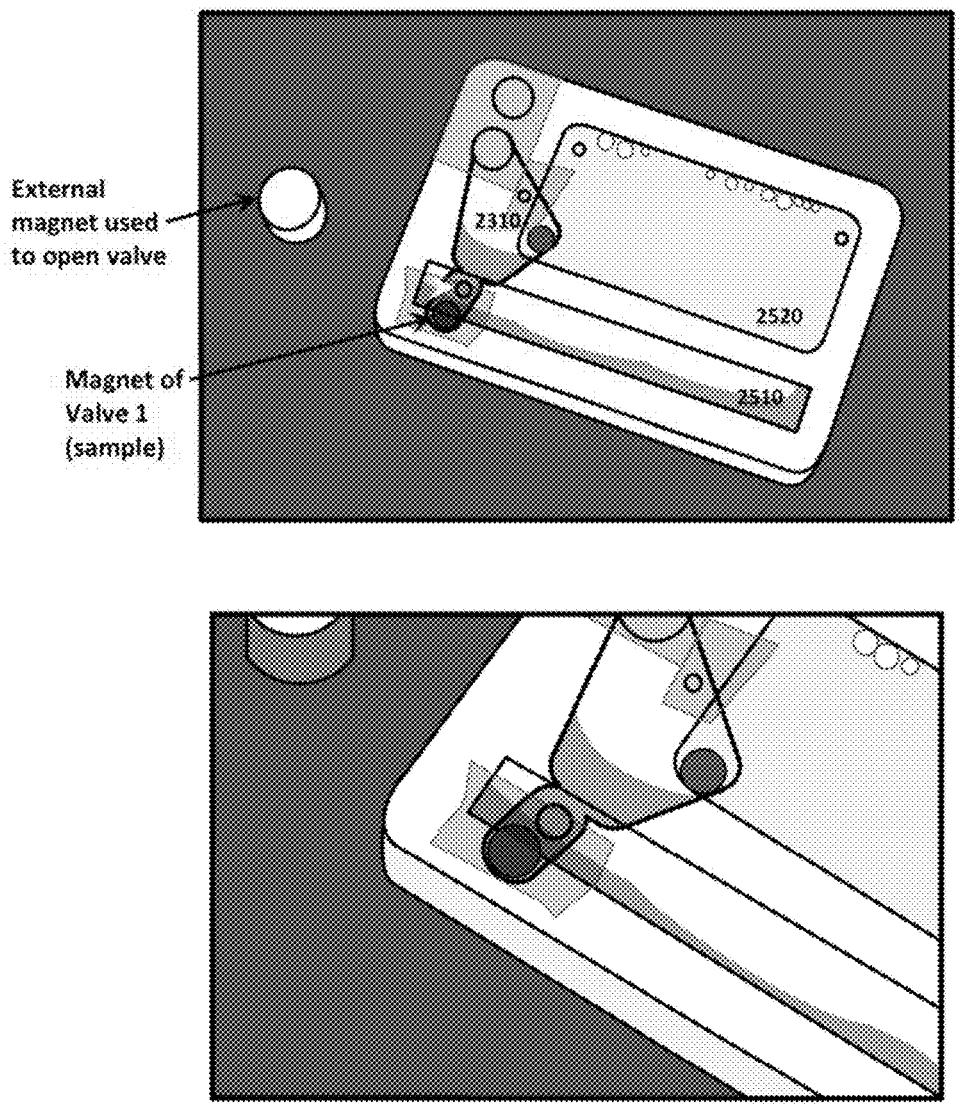
FIG. 4 provides top view schematics of an exemplary device after opening the sample valve ("Valve 1"). Shown are the magnet of Valve 1 (labeled with black arrow), the open via for this valve (indicated by white arrowhead), and the external magnet used to open the valve (labeled with black arrow).
Figure 5:
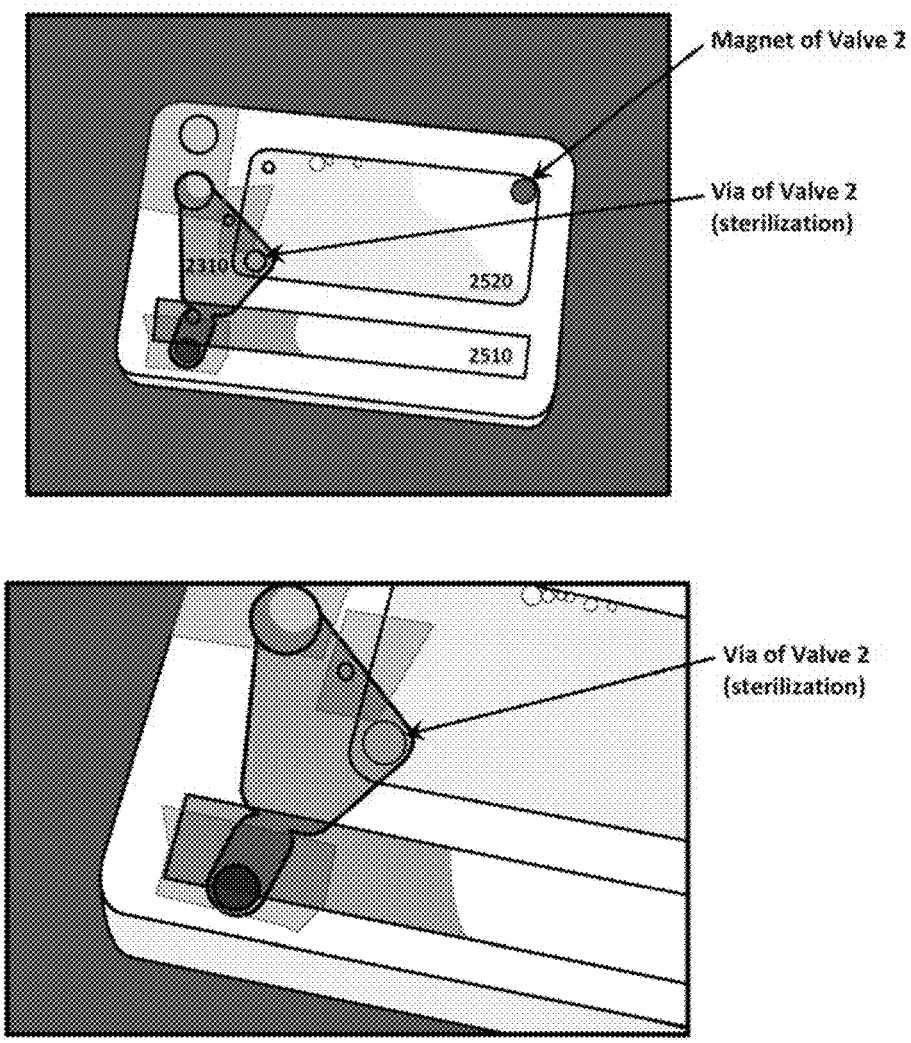
FIG. 5 provides top view schematics of an exemplary device after opening the sterilization valve ("Valve 2"). Shown are the magnet of Valve 2 (labeled with black arrow) and the open via for this valve (labeled with black arrow).
Figure 6:
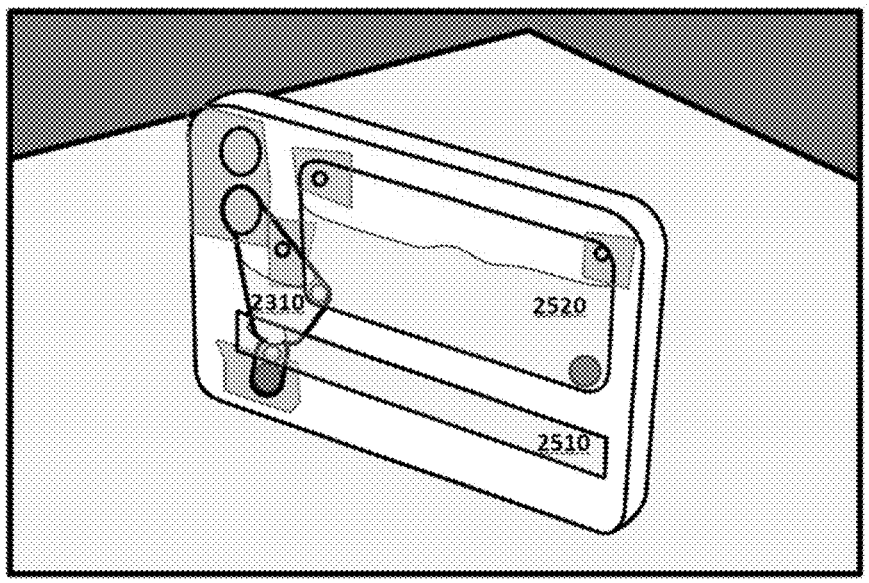
FIG. 6 provides elevational view schematics of an exemplary device after mixing of the sterilization solution in the sample chamber 2310 and the LFA chamber 2510. Shown in the sterilization chamber 2520 is the magnet of the sterilization valve (at lower right corner of this chamber). As can be seen, the sample chamber 2310 is designed to allow the magnet of the sample valve to rest in a recess (at lower left corner in the bottom schematic). In this manner, the magnet does not block flow within the LFA chamber 2510.
Figure 6:
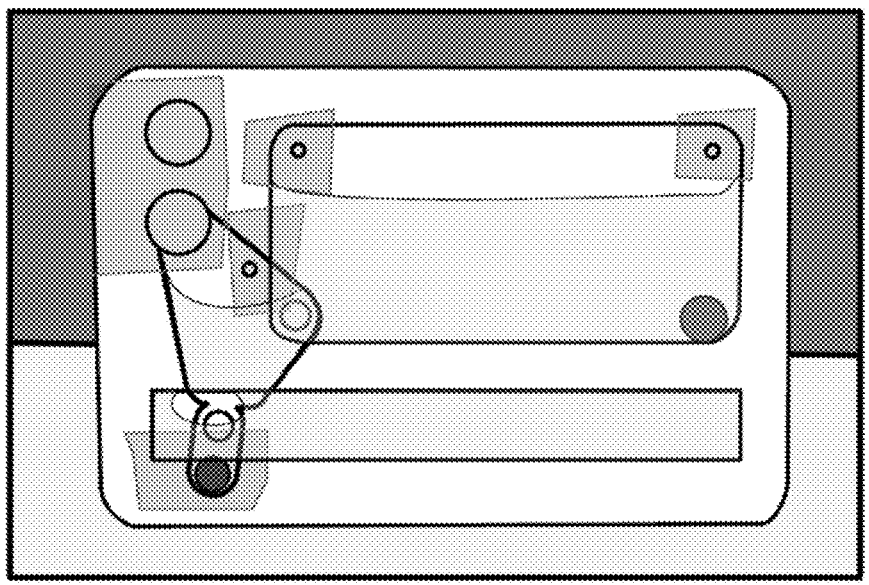

FIG. 3 provides top and bottom views of a prototype device denominated "Sample 1" before any valves 2450, 2460 are opened. FIG. 4 provides top views of the same device, at different levels of magnification, after the sample valve has been opened and liquid has begun to flow into the LFA chamber 2510. FIG. 5 provides top views of the same device, at different levels of magnification, after the sterilization valve has been opened and bleach has begun to flow from the sterilization chamber 2520 into the sample chamber 2310 and LFA chamber 2510. FIG. 6 provides an elevational view (top side facing the camera) of the same device, stood on an edge, after substantially complete intermixing of the bleach solution with the contents of the sample 2310 and LFA 2510 chambers.

Figure 7:
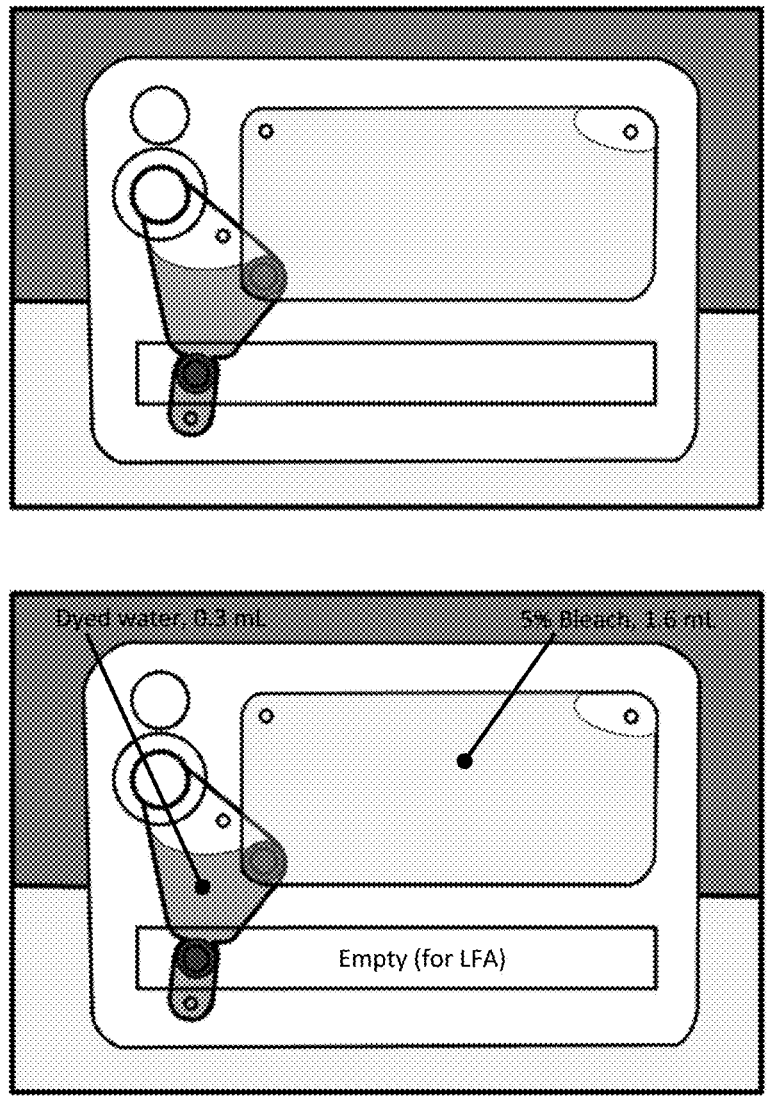
FIG. 7 provides front view schematics of an exemplary device for LFA.
Figure 8:
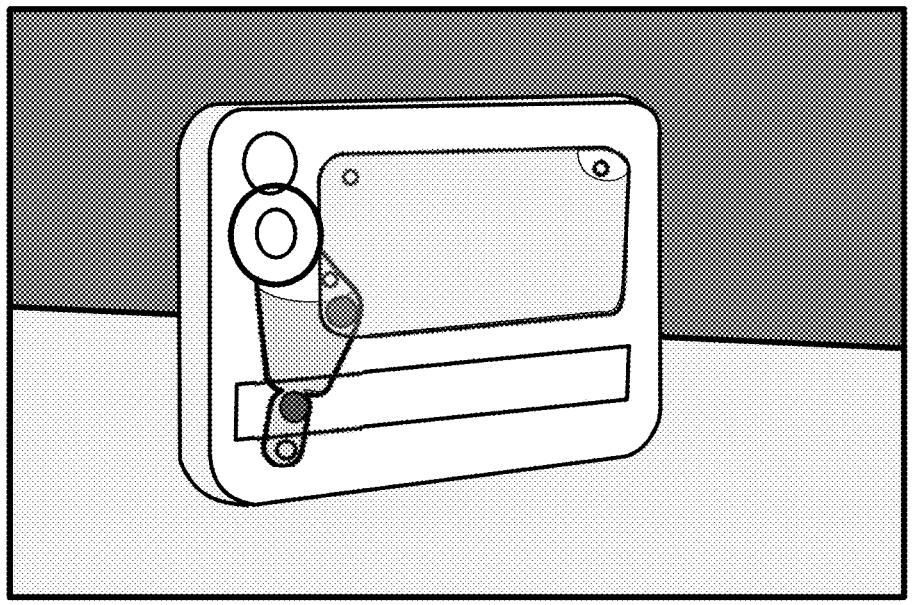
FIG. 8 provides side view schematics of an exemplary device with closed valves (top schematic and background of bottom schematic) and with open valves (foreground of bottom schematic).
Figure 8:
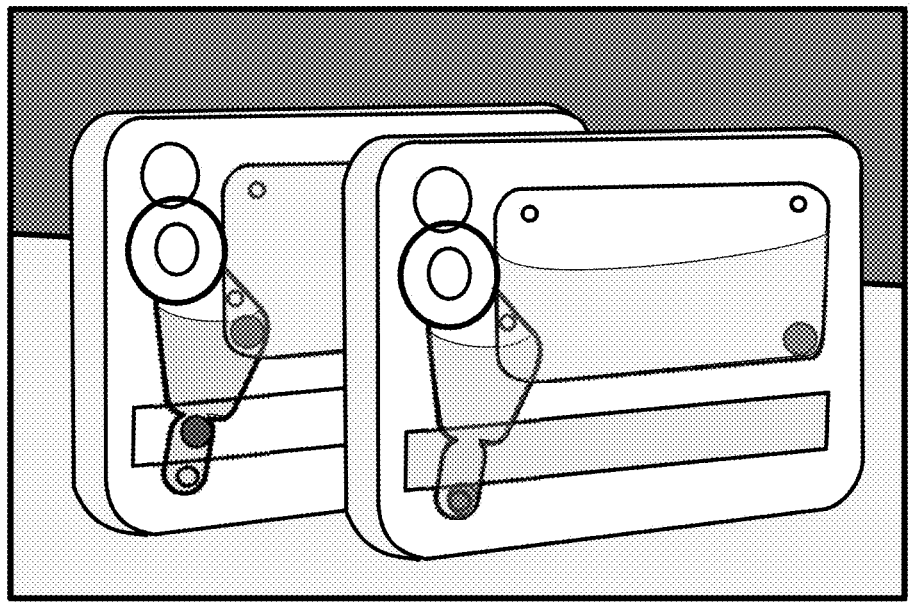

FIG. 7 provides a view, similar to the view of FIG. 6, of a second prototype device, denominated "Sample 2", prior to opening any valves. As indicated in the figure, the sample chamber contains 0.3 mL of dyed water, the sterilization chamber contains 1.6 mL of a 5% bleach solution, and the LFA chamber is empty. FIG. 8 provides in the top image and in the background of the bottom image a view of Sample 2 similar to the view of FIG. 7. FIG. 8 also provides for comparison, in the foreground of the bottom image, a view of Sample 1 similar to the view of FIG. 6.

Figure 9A:
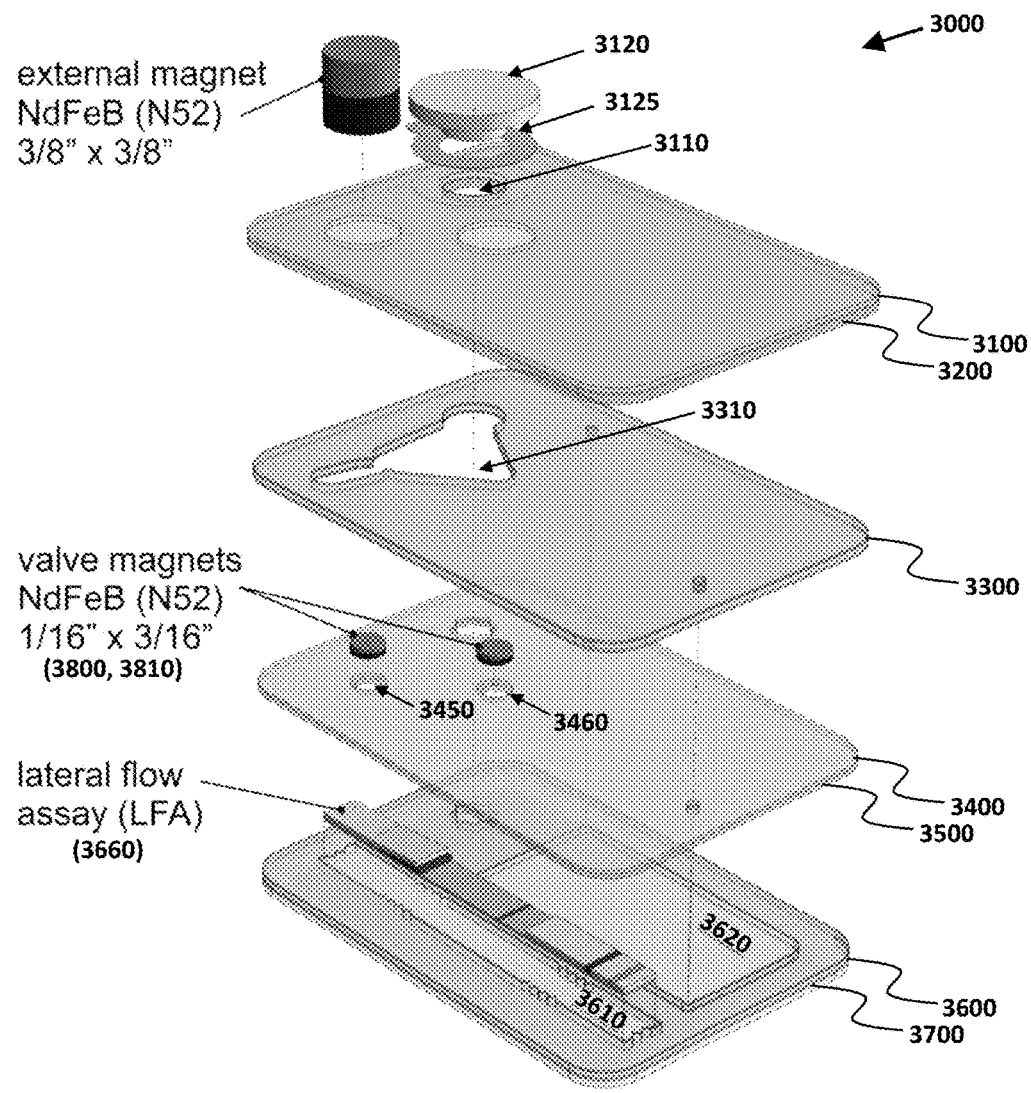
FIG. 9A-9B provides a perspective, exploded view of the various layers that were assembled to create an illustrative prototype 3000 embodying an aspect of the present invention.

In another example, the device is designed to accommodate a microculture chamber for LFA analysis. As shown in FIG. 9A, the device 3000 can include seven layers 3100-3700 and contain two valves 3800/3450, 3810/3460 and three fluidic chambers 3310, 3610, 3620. The device can further include a plug 3120, a seal 3125, and a fill hole 3110. The chambers can include a microculture chamber 3310, a sterilization chamber 3620, and an LFA chamber 3610 for placement of an LFA capillary bed 3660.

Figure 9B:
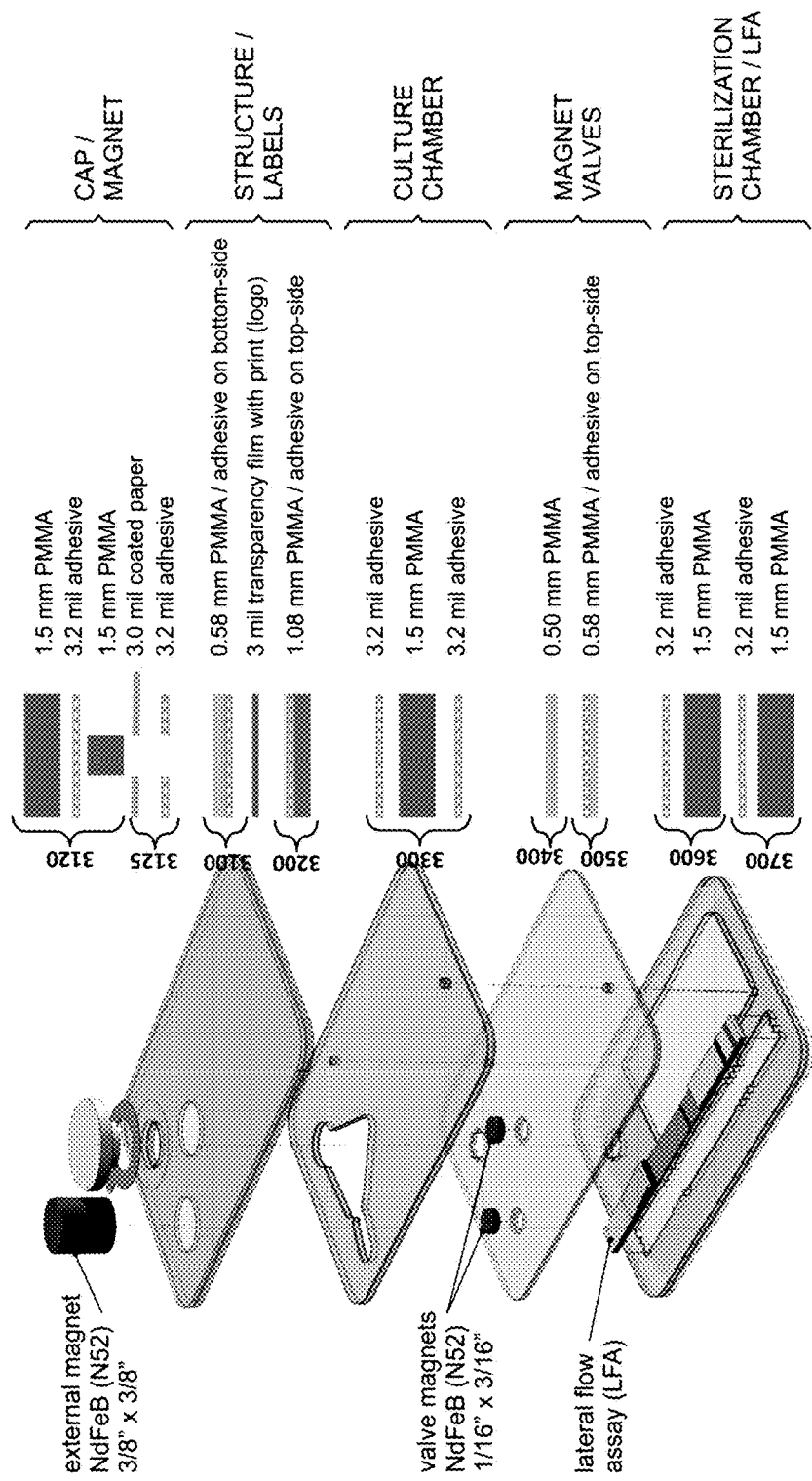
Figure 10:
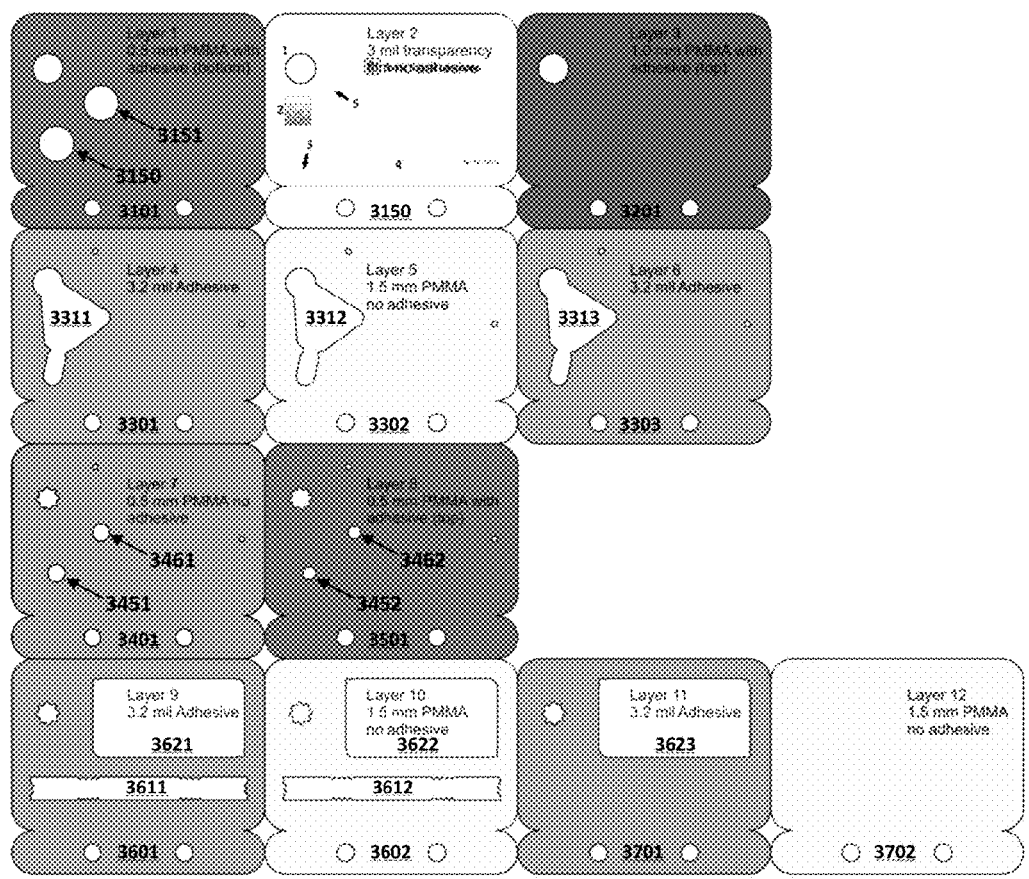
FIG. 10 provides a plan view of the respective layers in FIG. 9A-9B.

As seen in FIG. 9B, each of the layers in FIG. 9A can include further substrates. FIG. 10 shows a plan view of these substrates. The first layer 3100 can include a structural substrate 3101 having recessed regions 3150, 3151 for placement of an external magnet and a label 3150. Recessed regions 3150, 3151 are aligned with the valve elements, such that placing the external magnet in recess 3150 will align this external magnet with the first valve element. Similarly, placement of the external magnet in recess 3151 will result in alignment with the second valve element. The second layer 3200 includes a structural substrate 3201. The third layer 3300 includes an adhesive film 3301, a structural substrate 3302, and another adhesive film 3303, where each has an opening 3311-3313 for the microculture chamber 3310.

The fourth layer 3400 includes a structural substrate 3401 having vias 3451, 3461, and the fifth layer 3500 includes a structural substrate having an adhesive film 3501 and vias 3452, 3462. The first valve is formed from vias 3451, 3452, where the via 3451 in the upper substrate 3401 is slightly larger than the via 3452 in the lower substrate 3501. The second valve is formed from vias 3461, 3462. Similar to the first valve, the second valve is designed having the via 3461 in the upper substrate 3401 to be slightly larger than the via 3462 in the lower substrate 3501. As both valves have a larger via in the upper substrate, both valves are actuated in the same direction.

The sixth layer 3600 includes an adhesive film 3601 and a structural substrate 3602, and the seventh layer 3700 includes an adhesive film 3701 and a structural substrate 3702. As can be seen, some of these layers include an opening for the sterilization chamber 3621-3623 and the LFA chamber 3611, 3612.

Valves

The present apparatus can include one or more valves to interconnect closed or open structures. The valves include at least a valve element, a valve seat disposed within the device, and an adhesive interface provided between a surface of the valve element and a surface of the valve seat. In particular, the valve includes two structural components to ensure a closed valve: (i) an adhesive bond between the adhesive interface with the valve element and valve seat and (ii) matching or near matching of the cross-sections between the valve element and valve seat. Furthermore, the valves can be designed to actuate in different directions (e.g., as described for the fourth layer in FIG. 2B) or in the same direction (e.g., as described for the valves in FIG. 10).

The valves can be positioned to interconnect two or more closed or open structures. Exemplary structures include a chamber or reservoir, a channel, a fill-hole, or a well. In some embodiments, the structure can be closed (i.e., completely enclosed by surrounding walls and optionally including one or more outlets, inlets, or vias for fluidic communication with other structures). In other embodiments, the structure can be opened, i.e., having one or more walls and also having one or more sides that open to the environment. In particular embodiments, the structure is a closed chamber or channel including one or more inlets, outlets, or vias, where each of the inlet, outlet, or via is connected to another closed chamber or channel. In this embodiment, the valve can be positioned to have a valve seat substantially surrounding the inlet, outlet, or via, such that the valve element sits within the valve seat and substantially blocks the inlet, outlet, or via in the closed position.

The valve element can be formed from any useful material that is responsive to an applied magnetic field, such as a magnetic material or a metal. Exemplary magnetic materials include a neodymium magnet (also known as NdFeB), a samarium-cobalt magnet, a ferrite magnet, an alnico magnet, or any other permanent magnets. Exemplary metals include iron, nickel, cobalt, gadolinium, neodymium, samarium, steel, magnetite, a ferrite, as well other metals, alloys, or composites thereof, and any capable of being magnetized. The valve seat can be formed from any useful material, e.g., such as any polymer described herein.

The adhesive interface can include any useful adhesive. Exemplary adhesives include a pressure sensitive adhesive (e.g., an acrylic, silicon, or acrylic-hybrid based adhesive optionally including a support layer), an acrylic adhesive, an acrylic-hybrid adhesive, a silicone adhesive, and/or an adhesion promoter (e.g., Dow Corning® 1200 primer, including light aliphatic petroleum solvent naptha, xylene, tetrapropyl orthosilicate, tetrabutyl titanate, ethylene glycol methyl ether, tetra (2-methoxyethoxy) silane, and/or ethylebenzene).

The valve can be actuated by any useful applied magnetic field. For instance, FIG. 1A shows an external permanent magnet to actuate the valve element by applying an external magnetic field, but other sources for providing or inducing a magnetic field can be used. Exemplary sources include a permanent magnet, a magnetic coil (e.g., a solenoid), a metallic element to attract the valve element, and an electromagnet (e.g., an integrated electromagnet configured to be activated electronically).

The source providing the applied magnetic field can be an external source or a source that is integrated with the device. For instance and without limitation, an exemplary external source is provided in FIG. 1B, where the external magnet (or external source) applies a magnetic field to the valve (e.g., a thin disk magnetic valve 805 in this figure). In another instance, the source can be integrated with the device. For example and without limitation, the integrated source is provided within a layer of the device. In another embodiment, the integrated source is embedded between two or more layers within the device. Accordingly, any of the sources described herein (e.g., a metallic element to attract the valve element, an electromagnet, etc.) can be an external source or an integrated source.

In some embodiments, the integrated source is an integrated electromagnet configured to be activated electronically (e.g., configured to include one or more electrical components, such as an electrode, a power source, a wire, etc., where activation of the electrical component induces current that activates the electromagnet). Such an integrated electromagnet can be configured in any useful manner (e.g., provided within a layer of the device or embedded between two or more layers within the device, as well as positioned above the valve element, thereby allowing the valve element to respond to the applied magnetic field from the activated electromagnet). Exemplary integrated electromagnets include one or more magnetic particles (e.g., a thin membrane or layer including a magnetic nanocomposite material or bead, such as a rare earth magnetic powder, including an Nd—Pr—Ce—Fe—B alloy (e.g., MQP-12-5 isotropic powder), an Nd—Fe—B alloy, an Nd—Pr—Fe—B alloy, an Nd—Co—Fe—B alloy, an Nd—Ce—Fe—B alloy, an Nd—Pr—La—Fe—B alloy, an Nd—Nb—Fe—B alloy, a Pr—Fe—B alloy, or a Pr—Co—Fe—B alloy), one or more magnetic layers, or a solenoid electromagnet, where each can optionally further include one or more electrical components to activate the integrated electromagnet (e.g., one or more electrodes, such as micropatterned electrodes; a wire; or a power source, such as an AC or DC power source) or one or more magnetic field concentrators.

Reservoirs and Chambers

The present apparatus can include one or more reservoirs or chambers, which can be designated for a particular use. The terms "reservoir" and "chamber" are used interchangeably. Particular uses for such reservoirs and chambers include a sample chamber for receiving and/or storing a test sample, an incubation chamber for incubating a test sample (e.g., to amplify one or more targets and optionally containing media and/or host cells for such amplification), a reagent chamber containing one or more reagents for detecting one or more targets, a sterilization chamber containing one or more reagents to sterilize or disinfect the test sample (e.g., containing one or more sterilization agents, as described herein), an assay chamber for conducting one or more assays to detect one or more targets (e.g., an assay chamber containing a capillary bed for a lateral flow assay), and/or a waste chamber for storing one or more by-products of the assay. Each of these chambers can be interconnected by a valve (e.g., including a valve element and a valve seat) and/or a channel that can optionally include a valve in its fluidic path.

Further, these chambers can be configured to perform particular reaction steps. For instance, as shown in FIG. 11B, the device is labeled with numbers "1" to "5" to indicate the particular reaction steps, and the chambers are designed to allow these steps to be conducted in the indicated order. The first step (indicated by "1" on the upper left portion of the device in FIG. 11B) includes introducing the test sample to the sample port 4110 located at the upper portion of the culture chamber 4310. Second (indicated by "2" in this figure), the sample is incubated in the culture chamber 4310 containing the media (see FIG. 11A). Next (indicated by "3" in FIG. 11B), the LFA valve 4800/4450 is opened by applying an external magnet to the valve element (labeled "B" in FIG. 11A) and moving the valve element away from the via (in the direction of the black arrow in FIG. 11A). In this particular device, valve element B actuates by moving towards the top side of the device.

Then (indicated by "4" in FIG. 11B), the amplified sample flows into the LFA 4660 chamber for biodetection. Finally (indicated by "5" in FIG. 11B), the sterilization valve 4810/4460 is opened by applying an external magnet to the bottom side of the device, as this valve element actuates by moving towards the bottom side of the device. Upon opening this valve, bleach solution (or any sterilization agent, e.g., any described herein) in the sterilization chamber 4620 moves or flows into the culture chamber 4310 and the LFA 4660 chamber. The user may optionally shake or tap the device to facilitate mixing of the contents. In particular, if one or more agents are in solid form (e.g., a stabilized sterilization agent in powdered form), then flow of the agents into the chambers may be assisted by shaking and/or tapping the device.

Figure 11A:
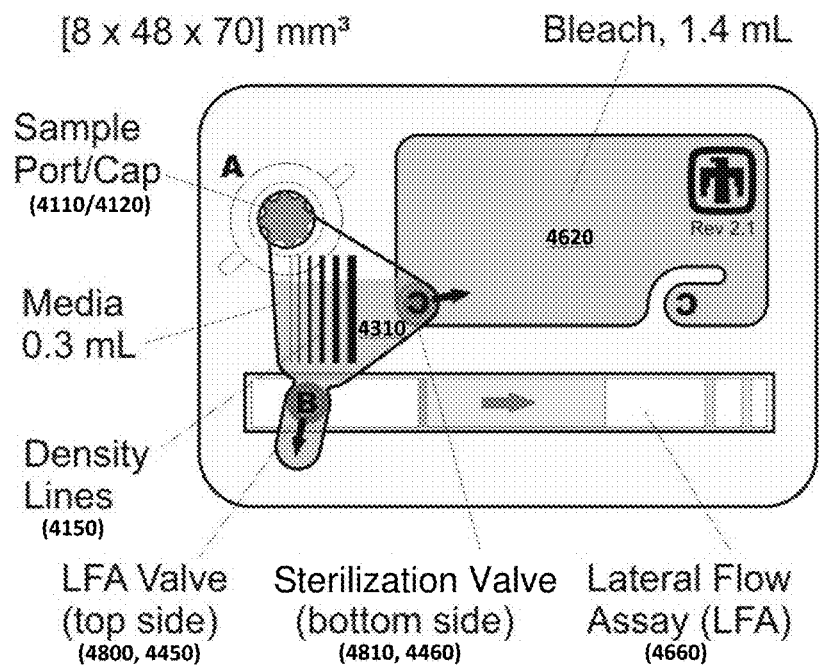
FIG. 11A-11B shows (A) a schematic and (B) a photograph of an exemplary fully assembled B. anthracis detection device with on-chip microculture for biological target amplification.
Figure 11B:
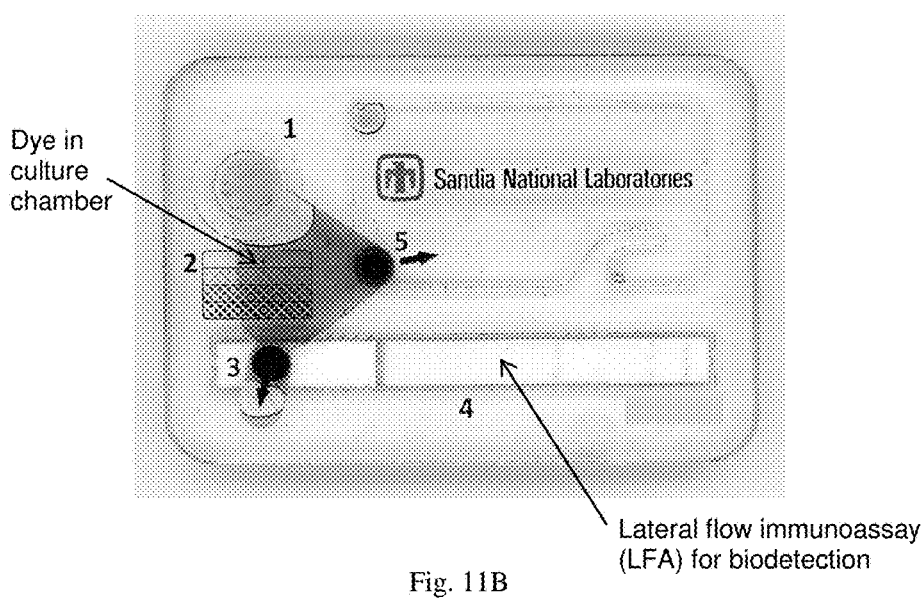

Optionally, the valve element for the sterilization valve can be placed in the position labeled "C" in the lower right portion of the sterilization chamber 4620 in FIG. 11A. In this position, the valve element possesses limited movement and does not block the flow of the bleach solution throughout the chambers in the device. In a similar manner, additional chambers and labels can be included to perform particular reactions in a particular order.

Multilevel Apparatus

The present apparatus can take any useful form, such as a multilevel apparatus having multiple layers. For instance, the apparatus can be configured to include one or more chambers, channels, and valves (including valve elements, valve seats, vias, and adhesive layers) in particular layers. These layers can be designed to optimize the mechanism of the valve, to accommodate multiple reaction steps in a plurality of chambers, to simplify production of the device, as well as any other design considerations.

The multilevel apparatus can include one or more components to facilitate assembly or usage of the apparatus. For instance, adhesive layers can be used between any structural layers to facilitate laminating and assembling of the device. In another example, alignment holes or markings can be used to position layers and openings in an appropriate manner. Such a device can include one or more labels to direct the user.

Furthermore, the multilevel apparatus can be designed to include valves that actuate in the same direction or in different directions. For instance, substrates 3401, 3501 in the device of FIG. 10 are designed to have larger vias in the upper substrate 3401 and smaller vias in the lower substrate 3501. In this manner, both valves actuate in the same direction (i.e., toward substrate 3103 or the top side of the assembled apparatus). As shown in FIG. 9A, both valve elements 3800, 3810 sit on a valve seat on the top side of the layer 3400.

In another embodiment, the valves actuate in different directions. For instance, as seen in FIG. 2B, substrates 1401-1403 are designed to have valve seats on opposing sides of the layer, where the larger via 1451 for the first valve is in the upper substrate 1401, but the larger via 1463 for the second valve is in the lower substrate 1403. As shown in FIG. 2A, the first valve element 1800 sits on a valve seat on the top side of layer 1400, and the second valve element 1810 sits on a valve seat on the bottom side of the same layer 1400. In this manner, the valves in a multilevel apparatus can be configured and operated in any useful way.

Multilevel or monolithic structures can be constructed using any useful method. Exemplary methods of fabrication include rapid prototyping, microfabrication (e.g., by casting, injection molding, compression molding, embossing, ablation, thin-film deposition, and/or Computer Numerically Controlled (CNC) micromachining), photolithography, etching techniques (e.g., wet chemical etching, reactive ion etching, inductively coupled plasma deep silicon etching, laser ablation, or air abrasion techniques), methods for integrating these structures into high-throughput analysis equipment (e.g., integration with a microplate reader or a control instrument, such as a computer), methods for fabricating and integrating valves (e.g., one or more pneumatic valves), methods for integrating structures with a transducer array, methods for modifying surfaces (e.g., by including a layer of extracellular matrix components, such as fibronectin (FN), laminin, Matrigel™, and/or RGD peptide), methods for including one or more capture arrays (e.g., a capture array including one or more capture agents provided in a high-density array on a substrate), and methods for providing vias or inlets (e.g., by piercing, drilling, ablating, or laser cutting), such as those described in U.S. Pat. No. 8,257,964; and U.S. Pub. Nos. 2012/0231976, 2012/0214189, 2011/0129850, 2009/0251155, and 2009/0036324, each of which is incorporated herein by reference in its entirety.

Materials

The present apparatus can be formed from any useful material. Exemplary materials include a polymer, such as polymethyl methacrylate (PMMA), polyethylene terephthalate (PET, e.g., biaxially-oriented PET or bo-PET), an acrylic polymer, poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof; silicon; glass; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organo-tin compounds), antioxidants (e.g., phenols or amines), and/or UV stabilizers (e.g., benzophenones or salicylates). Such materials can be provided in any useful form, such as in one or more layers that can be laminated to provide the assembled apparatus.

Targets and Samples

The present apparatus can be used to detect any useful targets. Exemplary targets include a bacterium, such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus*, Gonorrheae, *Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, chlamydia psittaci, Coxiella burnetii, Mycoplasma* (e.g., *M. mycoides*), etc.; allergens, such as peanut dust, mycotoxins, mold spores, or bacterial spores such as *Clostridium botulinum* and *C. perfringens*; toxins, such as ricin, mycotoxin, tetrodotoxin, anthrax toxin, botulinum toxin, staphylococcal entertoxin B, or saxitoxin; a virus, such as Adenoviridae (e.g., adenovirus), Arenaviridae (e.g., Machupo virus), Bunyaviridae (e.g., *Hantavirus* or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania*, or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); a fungus, such as *Aspergilli, Candidae, Coccidioides immitis*, and *Cryptococci*; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; a lipopolysaccharide; a salt; or an ion. Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), Filoviridae (e.g., Ebola virus and Marburg virus), Arenaviridae (e.g., Lassa virus and Machupo virus), *Clostridium perfringens*, any food-borne pathogen (e.g., *Salmonella* species, *Escherichia coli* O157:H7, or *Shigella*), *Chlamydia psittaci, Coxiella burnetii, Staphylococcal aureus, Rickettsia* (e.g., *R. prowazekii* or *R. rickettsii*), *Alphavirus* (e.g., Venezuelan equine encephalitis virus, eastern equine encephalitis virus, or western equine encephalitis virus), *Vibrio cholerae, Cryptosporidium parvum, Henipavirus* (e.g., Nipah virus), Bunyaviridae (e.g., *Hantavirus* or Rift Valley fever virus), Flaviviridae (e.g., Japanese encephalitis virus and Yellow fever virus), and *Coccidioides* spp.

The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), an environmental sample, etc.

Reagents

The present apparatus can include any number of useful reagents on-chip. Exemplary reagents include a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid, such those encoding for the protective antigen and/or capsule of *B. anthracis*)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a cell medium (e.g., selective media or other additives to select for or give advantage to a particular biological target during microculture, including agar, such a nutrient agar, blood agar, heart-infusion agar, where any of these can optionally include 5-7% horse or sheep blood agar; selective media, such as PLET (polymyxin B-lysozyme-EDTA-thallous acetate) agar for *B. anthracis*; nutrient media; minimal media; differential media; nutrient broth; or brain-heart infusion broth, where any of these can optionally include one or more antibiotics to select for or against particular targets, one or more nutrients (e.g., a carbon source, such as glucose), one or more enzymes, one or more host cells, and/or one or more salts), a detergent (e.g., sodium dodecyl sulfate (SDS)), a surfactant (e.g., Tween 20, Triton X-100, glycerin, polyvinylalcohol (PVA), polyvinylpyrrolidone (PVP), or polyethylene glycol (PEG)), a buffer (e.g., a phosphate or borate buffer), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

In some embodiments, the device or method includes a stabilized sterilization agent. For example and without limitation, the stabilized sterilization agent includes one or more chelators (e.g., chelators for one or more metal ions, which can decompose one or more sterilization agents, such as an aromatic amine), detergents, surfactants (e.g., a nonionic, cationic, or anionic surfactant), alkaline agents (e.g., urea), preservatives (e.g., ethylenediamine tetra acetic acid compounds), scavenging agents (e.g., free radical scavenging agents, such diarylamines or substituted dihydroquinolines), sequestrants (e.g., organic phosphonic acid), stabilizers (e.g., pyrophosphate, pyrophosphoric acid, dipicolinic acid, acetic acid, propionic acid, sulfonates, sulfates, phosphates, organic peroxycarboxylic acid, a stannate compound, organic phosphonic acids, amine-substituted phosphonic acids, alkyleneaminomethylene phosphonic acids, carboxylic acid substituted N-containing heterocyclics, aminopolycarboxylic acids, polyaminocarboxylic acids, tin-based compounds, phosphoric acids, alkylbenzene sulfonates with 6-18 carbon atoms, alkyl sulfates, and water-soluble salts of these acids), and/or buffers to inhibit or reduce decomposition of the sterilization agent. Exemplary stabilized sterilization agents include stabilized hydrogen peroxide agents, stabilized peracetic acid, and stabilized hydrogen peroxide-peracetic acid agents, which can optionally include one or more stabilizers (e.g., any described herein). Additional stabilized sterilization agents are described in U.S. Pat. Nos. 2,347,434; 2,590,856; 2,609,391; 4,051,058; 5,656,302; and U.S. Pub. No. 2010/0021558, each of which is incorporated by reference herein in its entirety.

In other embodiments, the stabilized sterilization agent is provided in a form that increases storage life. Such forms include powder, granule, pellet, gel, lyophilized, freeze-dried, and/or foam forms of the sterilization agent. Such forms can optionally include one or more chelators, detergents, surfactants, alkaline agents, preservatives, scavenging agents, sequestrants, stabilizers, and/or buffers, such as any described herein.

In some embodiments, the device or method includes an electroactive or electrocatalytic detection agent or label. Such electroactive or electrocatalytic agents include any compound or chemical capable of producing a redox (reduction/oxidation) reaction in which electrons are used or produced, thereby changing the properties of electron flow/transfer (e.g., conduction, resistance, capacitance, etc.), and being used for electrochemical detection. Exemplary electroactive or electrocatalytic detection agents and labels include a redox enzyme (e.g., horseradish peroxidase or glucose oxidase), a mediator chemical (an 'electron shuttle'), a nanoparticle (e.g., a catalytic nanoparticle, such as those including palladium or palladium-gold that can catalyze the redox reaction, or a detectable nanoparticle, such as gold or platinum nanoparticles), a redox active chemical (e.g., ferricyanide, ferrocene, ruthenuim bipyridine, etc.), as well as combinations of any of these with one or more antibodies or capture agents (e.g., where one or more catalytic nanoparticles, redox enzymes, or redox active chemicals are directly or indirectly attached (e.g., by a linking agent or a conjugate pair (e.g., biotin-avidin)) to antibodies or other capture reagents, where such combinations can be detected at an electrode). In particular embodiments, such electroactive or electrocatalytic agents are immobilized on one or more electrodes (e.g., on an electrode array of the device). Exemplary electroactive or electrocatalytic agents are described in Harper J C et al., "Selective immobilization of DNA and antibody probes on electrode arrays: simultaneous electrochemical detection of DNA and protein on a single platform," *Langmuir* 2007 Jul. 31; 23(16):8285-7; Polsky R et al., "Electrically addressable diazonium-functionalized antibodies for multianalyte electrochemical sensor applications," *Biosens. Bioelectron.* 2008 Jan. 18; 23(6):757-64; and Polsky R et al., Reagentless electrochemical immunoassay using electrocatalytic nanoparticle-modified antibodies," *Chem. Commun. (Camb.)* 2007 Jul. 14; (26):2741-3, each of which is incorporated herein by reference in its entirety.

In some embodiments, the cell medium further includes one or more living cells. For example, when the target is a virus, then the cell medium can include living cells or host cells to allow the virus to infect and/or multiply. Exemplary cells include a bacterium, a fungus, a mammalian cell, a plant cell, a eukaryote, a prokaryote, etc. In further embodiments, the cell medium is a stabilized cell medium (e.g., cell medium in powder, granule, pellet, gel, lyophilized, freeze-dried, and/or foam forms).

Additional Components

The present apparatus can include one or more additional components, as described herein. For instance, one or more detection components that allow for detection by electrochemical, colorimetric, fluorescent, western blot, immunohistochemistry, immunoassay (e.g., lateral flow assay), immunochromatography, radio immunoassay, optical immunoassay, enzyme immunoassay, and chemiluminescence, and/or electrochemiluminescence methods in any useful format. Exemplary detection components include a capillary bed, e.g., a lateral flow assay strip having a membrane to bind one or more capture agents, such as any described herein; a transducer, such as an optical sensor (e.g., including measuring one or more of fluorescence spectroscopy, interferometry, reflectance, chemiluminescence, light scattering, surface plasmon resonance, or refractive index), a piezoelectric sensor (e.g., including one or more quartz crystals or quartz crystal microbalance), an electrochemical sensor (e.g., one or more of carbon nanotubes, electrodes, field-effect transistors, etc.), an ion selective electrode, an ion sensitive field effect transistor (e.g., a n-p-n type sensor), a light addressable potentiometric sensor, an amperometric sensor (e.g., having a two-electrode configuration (including reference and working electrodes) or a three-electrode configuration (including reference, working, and auxiliary electrodes)), an impedimetric sensor, a disk electrode, a spherical electrode, a plate electrode, a hemispherical electrode, a planar electrode, a three-dimensional electrode, a porous electrode, a post electrode, a microelectrode (e.g., having a critical dimension on the range of 1 to 1000 μm, such as a radium, width, or length from about 1 to 1000 μm), or a nanoelectrode (e.g., having a critical dimension on the range of 1 to 100 nm, such as a radium, width, or length from about 1 to 100 nm), as well as arrays thereof; fiber optics, such as for excitation and collection for fluorescence detection; and/or integrated wave-guides, circular or elliptical microlenses, and/or photodiodes, as well as arrays thereof.

In particular embodiments, the LFA strip includes a sample pad at the proximal end of the strip to receive the sample from an open valve; a conjugate pad downstream of the sample pad and including one or more capture agents that bind to the target in the sample, thereby forming a complex, where the capture agent is optionally embedded in a dissolvable matrix; a capillary bed downstream of the conjugate pad and configured to receive the complex, if present, where the capillary bed is a membrane and includes a test area having one or more specific detection agents that bind to the complex; and an absorption pad at the distal end for absorbing excess sample volume. In further embodiments, the capillary bed includes a control area having non-specific detection agents that indicate sample flow to the distal end of the strip. In some embodiments, the capture agent is a particle (e.g., a nanoparticle) conjugated to an antibody specific for the target, and the specific detection agent is an antibody specific for the target. In further embodiments, the non-specific detection agent is a control antibody that non-specifically binds the complex.

The device can include one or more separation/extraction components (e.g., filters, posts, membranes, weirs (optionally including beads), matrices, or high voltage electrodes for performing on-chip capillary electrophoresis separations); heating components (e.g., electrodes or filaments); pumps (e.g., active or passive pumps, such as a low flow rate peristaltic pump or application of negative pressure, such as by actuating a valve); a membrane (e.g., placed within a channel and/or a chamber); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); a resistance-based temperature sensor; a photodetector; a photovoltaic cell; a diode; one or more components to operate a transducer, such as a power source to operate an electrode; a data-processing circuit powered by the power source and electrically connected to the transducer (e.g., a counter electrode, a reference electrode, and at least one said working electrode); and/or one or more components for autonomous remote monitoring of a sample, such as an analog-to-digital converter, a radiofrequency module, and/or a telemetry unit (e.g., configured to receive processed data from a data-processing circuit electrically connected to the detection component and to transmit the data wirelessly).

Kits

The present apparatus can further be provided in a kit. The kit can include one or more of the following: a collection swab for collecting the test sample, a source for actuating the valve(s) (e.g., an external permanent magnet), an external heater for incubating the test sample within the apparatus, a detection component (e.g., a light-emitting diode and/or a photodiode), a power source (e.g., when the device includes one or more electrically activatable component, such as an electromagnet), and/or a telemetry unit (e.g., any described herein).

Methods of Use

The present apparatus includes one or more valves that can be integrated with any assay for detecting any target of interest. In particular embodiments, the target is a biological agent that can be amplified, and the apparatus is adapted to be a microculture device, which can optionally further include a component for detecting the presence of one or more targets.

In particular embodiments, the apparatus includes a culture chamber on-chip, as well as other structures to maintain or test this culture. For instance, the apparatus can include specific fabrication methods and/or microfluidic geometries to deliver cell media and nutrients or to promote microcirculation in a bioreactor (e.g., by using negative pressure); integration of cell culture chambers with an array of electrodes (e.g., to monitor cell migration); and/or maintenance of cell viability under various controllable conditions for basic studies of cellular growth/behavior using external devices (e.g., a microscopes) to monitor cells. Such an apparatus can include a microwell, e.g., as described in U.S. Pat. No. 8,257,964; a perfusion system, e.g., as described in U.S. Pub. No. 2012/0231976; an electrode array, e.g., as described in U.S. Pub. No. 2009/0251155; a sensor, e.g., as described in U.S. Pub. No. 2011/0129850; a module to measure or detect general metabolites/byproducts from known cells under well-controlled conditions, e.g., as described in U.S. Pub. No. 2012/0214189; a biodetection or detection components including a capture agent, e.g., in a high-density barcode array form, as described in U.S. Pub. No. 2009/0036324, where the barcode array can be used to detect multiple proteins and/or genes from a single cell via on-chip single cell culture, lysis, mRNA, and protein isolation/purification, such as those in an integrated microfluidic device described in U.S. Pub. No. 2009/0053732; methods for controlling channel resistance or flow rate for use with one or more capture agents, e.g., as described in U.S. Pub. Nos. 2009/0053732 and 2013/0224729; methods for biodetection using probes for target DNA, e.g., methods for determining phenotype using molecular inversion probes, as described in U.S. Pub. No. 2013/0224729; methods for detecting proteins, e.g., methods for detecting nascent proteins by using primers encoding for N- or C-terminal markers, as described in U.S. Pat. No. 8,278,045 and U.S. Pub. No. 2011/0250609; and/or use of fluorogenic compounds as detecting agents, e.g., use of FRET-based compounds that are cleavable by one or more enzyme, such as those described in U.S. Pat. Nos. 6,566,508 and 6,372,895. Furthermore, such apparatuses can be desirable for basic science studies in cell biology, pharmacology, and immunology. For example, such apparatuses can be amenable to high-throughput screening of drugs on living cells.

Further exemplary uses and components to effect such uses are provided in U.S. Pat. Nos. 6,566,508, 6,372,895, 8,257,964, and 8,278,045; U.S. Pub. Nos. 2009/0036324, 2009/0053732, 2009/0251155, 2011/0129850, 2011/0250609, 2012/0214189, 2012/0231976, and 2013/0224729; Int. Pub. Nos. WO 01/14578, WO 2008/079320, and WO 2009/012340; and EP Pub. Nos. 1204671, 1210449, 2108955, 2167634, and 2464753, each of which is incorporated herein by reference in its entirety.

In particular embodiments, the present apparatus include use of a cell culture to amplify the biological target (e.g., not just maintain cell viability or maintain well-controlled culture conditions); and use of an unknown sample and detecting the cells themselves or highly specific metabolites/byproducts to identify the presence or absence of a particular cell in the original unknown sample. These characteristics are fundamentally different than a platform for maintaining cell viability for various biological studies.

EXAMPLES

Example 1: Prototype Device

We will now provide fabrication details for prototype devices that were made and tested. As explained below, the devices were laminated from sheets of polymethyl methacrylate (PMMA) and biaxially-oriented polyethylene terephthalate (bo-PET, often marketed under the tradename "Mylar™"). The various perforations were cut out using a carbon dioxide laser cutter. Lamination was performed under pressure using a hydraulic press or roller press. The valve elements were pressed onto their adhesive-coated seats using the hydraulic press.

The adhesive used for the valve seats was an acrylic-based adhesive marketed by Adhesives Research of Glen Rock, Pa., under the product number ARCARE-90445. To achieve a desired amount of adhesion between the valve element and the valve seat, a controlled amount of pressure was applied for a controlled time duration. Further details are provided below. It should be noted in this regard that the amount of adhesion is also dependent on the contact surface area between the adhesive layer and the valve element, and that for that reason, our process parameters should be adjusted for design variations in which that area is modified.

The valve element was a cylindrical N-52 magnet (composed of neodymium-iron-boron alloy) 0.1875 inch in diameter and 0.0625 inch in height. The external magnet used for manual actuation was a cylindrical N-52 magnet 0.375 inch in diameter and 0.375 inch in height.

FIGS. 9A-9B and 10 provide views of the various layers that were assembled to create the prototypes. FIG. 9A-9B is a perspective, exploded view of a prototype 3000, and FIG. 10 provides plan views of the respective layers. Beginning at the top and proceeding downward in sequence, the layers were as described below.

The cap assembly 3120 includes an upper ("cap") portion of 1.5 mm PMMA, a 3.2-mil layer of adhesive, and a lower ("stem") portion of 1.5 mm PMMA, followed by 3.0-mil coated paper and 31.2-mil adhesive (together 3125). The stem portion plugs the fill-hole 3110 in the underlying PMMA sheet.

A structural and legend-bearing assembly 3100, 3200 includes 0.5-mm or 0.58-mm PMMA 3101 coated on the bottom side with adhesive, a 3-mil transparency film 3150 of Mylar™ bearing such printed legends as might be desired, and 1.08-mm PMMA 3201 coated on the top side with adhesive. The PMMA substrate 3101 includes openings 3150, 3151 for placement of the external magnet so that it is aligned with one of the two valves.

The sample chamber (or "culture chamber") assembly 3300 includes a 1.5-mm sheet 3302 of PMMA perforated to define the sample chamber (including a side branch for disposition of its valve magnet after valve opening), preceded and followed by 3.2-mil adhesive layers 3301, 3303. The sample chamber 3310 is formed by openings 3311-3313.

The magnetic valve assembly 3400, 3500 includes an 0.50-mm PMMA sheet 3401 followed by an 0.5-mm or 0.58-mm PMMA sheet 3501 coated on the top side with adhesive, both sheets perforated to define the vias 3451, 3452, 3461, 3462 and valve seats 3450, 3460 for the respective sample and sterilization valve magnets 3800, 3810. In one embodiment, the vias 3452, 3462 are defined in the lower sheet 3501 and, as explained above, the upper sheet 3401 has slightly larger perforations 3451, 3461 so that the valve element will rest on a shoulder portion of the lower sheet 3501 and within the larger via in the upper sheet. In another embodiment, the upper sheet has a slightly smaller perforation (than the via in the lower sheet), such that the valve element will rest on a shoulder portion of the upper sheet and within the larger via in the lower sheet.

A sterilization chamber and LFA assembly 3600, 3700 includes a 1.5-mm PMMA sheet 3602 perforated to define the sterilization chamber 3620 (openings 3621-3623) and LFA chamber 3610 (openings 3611, 3612) and preceded and followed by 3.2-mil adhesive layers 3601, 3701, followed by a 1.5-mil PMMA structural base layer 3702. An absorbent sensor strip 3660 for use as an LFA capillary bed is placed in the LFA chamber and held in place by the overlying and underlying adhesive layers.

In an illustrative assembly procedure, the processing temperature was ambient temperature in the range 20-25° C. The processing pressure for adhesive lamination of sheet to sheet was about 3000 psi. The processing pressure for magnet to adhesive was 10-30 psi. The duration for application of pressure in each step for joining layers or for adhering a magnet was two minutes. We found that for optimal adhesion, the duration should be carefully controlled, because too little or too much time could result in poor adhesion. The area of each adhesive-to-magnet interface was 30.3 sq. mm.

Example 2: Amplification of Biological Targets Via On-Chip Culture for Biosensing Anthrax poses a significant threat to US National Security as demonstrated by the 2001 terrorist attacks targeting the US Postal Service and Hart Building. The causative agent, *Bacillus anthracis*, is ubiquitous, and more importantly, found in countries harboring terrorists. Between the years 2005-2012, more than three thousand *B. anthracis* outbreaks were reported. This is likely an underestimation of the incidence and prevalence of the disease. Anthrax commonly causes sudden death in livestock, and consequently, is routinely isolated and propagated by indigenous populations to diagnose the disease. This practice of isolation and propagation in labs with little-to-no security in countries harboring terrorists drastically increases laboratories' repositories of *B. anthracis*, and escalates the risk that the agent can be stolen for nefarious purposes. In order to mitigate this risk, a simple and inexpensive assay is needed to reduce the amount of *B. anthracis* handled in the laboratory and eliminate all viable organisms.

Despite significant progress made in the development of biosensor technologies the utility of many assays remains limited. Commonly, these assays suffer from the inability to detect the biological target at or below the infectious dose. For example, lateral flow assays (LFA) used for biodetection permit simple, one-step sample processing without the need for multiple washing and labeling steps, greatly simplifying point-of-use in the field. However, detection limits for LFAs range from $10^6$-$10^7$ cells/spores per mL sample. This sensitivity is not low enough to be practical, where the infectious dose is commonly $10^2$-$10^3$ cells/spores.

The vast majority of biodetection platforms rely on amplification of the biotarget (e.g., PCR amplification of DNA) or amplification of the signal (e.g., catalytic labels) to reach relevant detection limits. This typically requires devices to be complex, requiring washing and labeling steps, multiple reagents which may need refrigeration, power, and high skill to operate. These are undesirable attributes, especially in resource limited environments. Amplification of the biological target prior to downstream biodetection that is ultra-low cost and is very simple to operate can provide a transformational step in allowing existing bioassay technologies to detect practical concentrations/levels of the biological target.

Accordingly, we have developed a portable robust device for amplification of biological targets facilitating subsequent biodetection that is ultra-low cost, requires no power or instrumentation to operate, no cold chain (e.g., no refrigeration nor freezing) to maintain efficacy, and can be operated by individuals with little to no technical training. The self-contained credit-card sized device employs on-chip microculture methods to amplify the biological analyte prior to downstream detection, improving detection limits by more than four orders of magnitude (detection from $10^2$ spores/mL initial inoculum of *B. anthracis* demonstrated using downstream LFA).

Additionally, the device utilizes chemicals and bacteriophage to sterilize the contents following assay. Self-decontamination is critically important for minimizing potential malicious use of the amplified bacterial sample following assay. This device has the potential to prevent the currently common practice of isolation and propagation of biothreat agents by indigenous populations to diagnose disease in countries harboring terrorists.

This device can also be used for other applications including detection of food-borne bacteria (e.g., *E. coli, Salmonella*, etc.) and bacteria of medical interest (e.g., *Staphylococcus, Streptococcus*, Gonorrhoeae, etc.). This device can also detect multiple agents by modifying the downstream detection method to be multianalyte.

An exemplary device is provided herein. A plastic multilayered microfluidic device was prepared via $CO_2$ laser machining of plastic laminates by ablation. Acrylic adhesive coatings on the plastic sheets provided a route to multilayer structures via simple hydraulic pressing at room temperature (see FIG. 2A-2B). This approach allowed for rapid and inexpensive development of robust devices. FIG. 11A-11B provides an integrated on-chip culture and subsequent biodetection device. The device includes a sample port 4110 and cap 4120, which is connected to the microculture chamber 4310 including media and density lines 4150. A first valve (the LFA valve including a valve element 4800 and a via 4450) provides fluidic communication between the microculture chamber 4310 and the LFA chamber having the LFA capillary bed 4660. The second valve (the sterilization valve including a valve element 4810 and a via 4460) provides fluidic communication between the microculture chamber 4310 and the sterilization chamber 4620.

Fluid moves between chambers on different Z planes (3D) by simple shaking and/or tapping the device (FIG. 11A), and valves are actuated by use of an external magnet (FIG. 1B).

As shown in FIG. 11B, the device includes a culture chamber 4310 integrated with a lateral flow assay or lateral flow immunoassay (both referred to as LFA) 4660 for biodetection. The volume of this microculture chamber can be ~300 mL. The entire device, including the microculture chamber, remains sealed during the culturing period. Culture can be performed at room temperature, or at elevated temperatures, by placing the device in an incubator or in/near another heat source. Culturing period is variable depending on the composition of the sample and the culture matrix, but ranges typically between 24 and 72 hours.

As shown in FIG. 1B, the magnet valve is held in place by a thin adhesive ring, preventing access of the microculture solution in the upper chamber to the underlying LFA. An external magnet can be used to remove the magnet from the thin adhesive ring, exposing the vertical connection between the two chambers. A substance (e.g., liquid or solid) then transfers between chambers by simply shaking the device. This magnetic valve configuration is ultra-low-cost (about $0.19 per magnet), requires no power, is simple to operate, and allows assay contents to remain sealed within the device.

Live culture tests were conducted (FIG. 12A). With a 1000 spore inoculum, the sample was incubated at 37° C. with no agitation. After 24 hours, a visibly turbid culture was observed. Optionally, glass beads can be included in the culture chamber to aid in mixing prior to exposing the sample to the LFA strip. Following the assay, a sterilization solution can be used to destroy the culture. FIG. 12B provides a test experiment using a commercially available LFA strip, where *B. anthracis* was detected with 1000 spore inoculum, which was incubated at 37° C. with no agitation for 24 hours. This device provided a three orders of magnitude improvement in LFA detection limit.

Figure 13A:
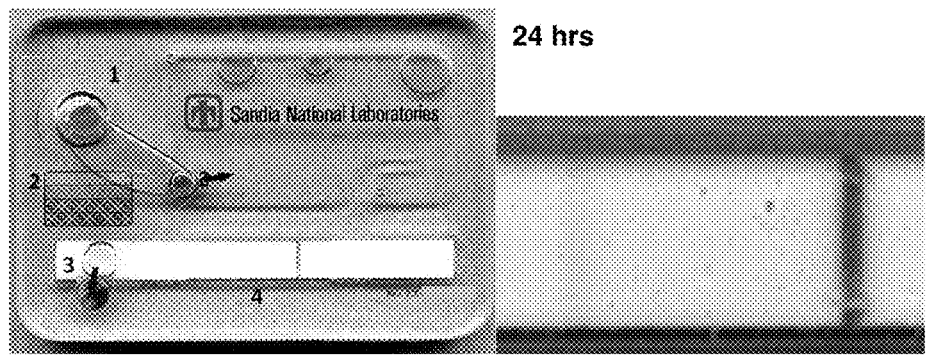
FIG. 13A-13C shows the effect of culture length on a lateral flow immunoassay (LFA) in exemplary B. anthracis detection devices. The initial spore count was an inoculation with 100 spores.
Figure 13B:
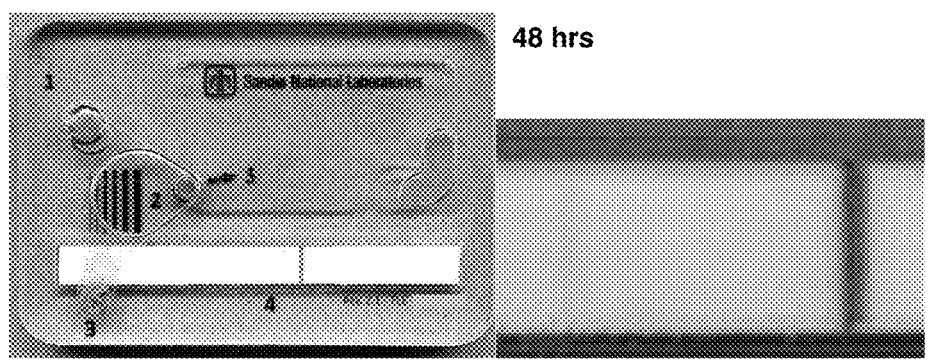
Figure 13C:
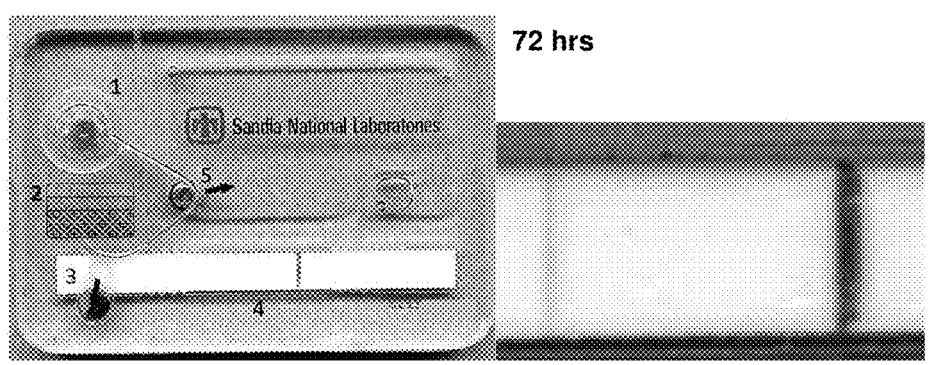

Lower spore counts were also detected. FIG. 13A-13C provides the results of experiments with a lower spore count of 100 spore inoculum and incubation at 37° C. Experiments were conducted with no agitation and using a commercially available LFA strip. The culture time included 24, 48, or 72 hours (in FIG. 13A-13C, respectively), and an additional development time of about 15 to 60 minutes for the LFA strips shown in FIG. 13A-13C. This device provided a four orders of magnitude improvement in LFA detection limit.

Various advantages are observed with this cartridge device. First, the device is simple to operate and interpret. Further, manufacturing costs are minimized by the low cost of the magnet actuated valves and prototyping of the device. In addition, the device is completely sealed, which reduces contamination of the assay system, handling of potentially caustic sterilization agents (e.g., the sterilization agent can be loaded during assembly, and the device can include no exit ports), and dispersing potentially hazardous biologics after culturing. As shown, the detection limit was improved by employing on-chip culture of the target inoculum. To minimize further exposure of anthrax to others, the device includes a chamber for subsequent sterilization of the culture.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for amplifying a target in a sample, the method comprising:
   introducing the sample within a first reservoir of a first apparatus, wherein the first apparatus is a microculture apparatus comprising:
   a first reservoir comprising at least one first outlet, wherein the first reservoir comprises a cell medium;
   a second reservoir, wherein the first outlet is configured for fluidic communication between the first and second reservoirs;
   a first valve element;
   a first valve seat conformed to support the first valve element in a position that closes the first outlet, wherein the first valve seat comprises a first via within which the first valve element rests and a second via, wherein a shoulder on which the first valve element rests is provided by an edge of the second via; and
   a first layer of adhesive deposited on at least a portion of the shoulder of the first valve seat and configured to releasably bond to a surface of the first valve element when seated in the outlet-closed position,
   wherein the first valve element is responsive to an applied magnetic field of sufficient strength by detaching from the first valve seat and undergoing a displacement that causes the first outlet to open; and
   incubating the sample within the first reservoir, thereby amplifying the target within the sample and providing an amplified sample.

2. The method of claim 1, further comprising sterilizing the amplified sample during or after the incubation step.

3. The method of claim 1, further comprising opening the first outlet by applying a magnetic field to the first valve element adhesively bonded to the first valve seat so as to produce a magnetic force configured to detach the first valve element from the first valve seat.

4. The method of claim 1, further comprising introducing the amplified sample within an assay chamber, wherein the first outlet leads to the assay chamber and the assay chamber is configured to include one or more detection agents for identifying the target, thereby identifying whether or not the target is present within the sample.

5. The method of claim 4, wherein the assay chamber is provided in the first apparatus or in a second apparatus having an inlet in fluidic communication with the assay chamber.

6. The method of claim 4, further comprising sterilizing the amplified sample after identifying the target.

7. The method of claim 6, wherein the sterilizing step comprises:
   opening a second outlet in fluidic communication between a second reservoir and the assay chamber, by applying a magnetic field to a second valve element adhesively bonded to a second valve seat conformed to support the second valve element in a position that closes the second outlet, wherein the magnetic field produces a magnetic force configured to detach the second valve element from the second valve seat; and
   introducing a sterilization agent from the second reservoir into the assay chamber.

8. The method of claim 7, wherein the fluidic communication between the second reservoir and the assay chamber occurs through an open passageway in the first reservoir.

9. The method of claim 4, wherein the detection agent is one or more of a dye, a particle, a marker, or a label.

10. The method of claim 9, further comprising measuring the presence of a detectable signal from the detection agent by electrochemical, colorimetric, fluorescent, western blot, immunohistochemistry, immunoassay, immunochromatography, radio immunoassay, optical immunoassay, enzyme immunoassay, chemiluminescence, and/or electrochemiluminescence methods.

11. The method of claim 10, wherein the measuring step comprises detection by lateral flow assay.

12. The method of claim 10, wherein the measuring step comprises detection of a plurality of targets.

13. The method of claim 12, wherein the plurality of targets includes one or more food-borne pathogens.

14. The method of claim 13, wherein at least one food-borne pathogen is selected from the group consisting of *Salmonella, Escherichia coli, Bacillus cereus, Clostridium botulinum, Listeria monocytogenes,* and *Yersinia*.

15. The method of claim 12, wherein the plurality of targets includes one or more weaponized pathogens.

16. The method of claim 15, wherein at least one weaponized pathogen is selected from the group consisting of *Bacillus anthracis, Yersinia pestis, Francisella tularensis, Brucella, Burkholderia mallei, Burkholderia pseudomallei,* and *Shigella.*

* * * * *